United States Patent
Kim et al.

(10) Patent No.: US 12,398,372 B2
(45) Date of Patent: Aug. 26, 2025

(54) METHOD FOR CULTURING CORD BLOOD-DERIVED NATURAL KILLER CELLS USING TRANSFORMED T-CELLS

(71) Applicant: GREEN CROSS LAB CELL CORPORATION, Yongin-si (KR)

(72) Inventors: Yusun Kim, Yongin-si (KR); Eun Ji Kim, Yongin-si (KR); Gyeong-Min Park, Yongin-si (KR); Bitna Yang, Yongin-si (KR); Bokyung Min, Yongin-si (KR); Sungyoo Cho, Yongin-si (KR); Yu Kyeong Hwang, Yongin-si (KR)

(73) Assignee: GC Cell Corporation, Gyeonggi-do Republic of (KR)

(*) Notice: Subject to any disclaimer, the term of this patent is extended or adjusted under 35 U.S.C. 154(b) by 314 days.

(21) Appl. No.: 17/293,835

(22) PCT Filed: Nov. 13, 2019

(86) PCT No.: PCT/KR2019/015469
§ 371 (c)(1),
(2) Date: May 13, 2021

(87) PCT Pub. No.: WO2020/101361
PCT Pub. Date: May 22, 2020

(65) Prior Publication Data
US 2024/0084256 A1    Mar. 14, 2024

(30) Foreign Application Priority Data

Nov. 14, 2018 (KR) .......... 10-2018-0139722
Nov. 13, 2019 (KR) .......... 10-2019-0145068

(51) Int. Cl.
*A61K 40/15* (2025.01)
*A61K 40/42* (2025.01)
*C12N 5/0783* (2010.01)

(52) U.S. Cl.
CPC ............ *C12N 5/0646* (2013.01); *A61K 40/15* (2025.01); *A61K 40/42* (2025.01); *A61K 2239/31* (2023.05); *A61K 2239/38* (2023.05); *A61K 2239/48* (2023.05); *C12N 2501/2302* (2013.01); *C12N 2501/515* (2013.01); *C12N 2502/1114* (2013.01); *C12N 2510/00* (2013.01)

(58) Field of Classification Search
CPC ............ C12N 5/0646; C12N 2501/515; C12N 2502/1114; C12N 2510/00; C12N 2501/2321; C12N 2501/25; C12N 2501/599; C12N 2502/1164; A61K 39/4613
See application file for complete search history.

(56) References Cited

U.S. PATENT DOCUMENTS

| | | |
|---|---|---|
| 5,882,650 A | 3/1999 | Ennis |
| 9,062,287 B2 | 6/2015 | Ideno et al. |
| 9,834,753 B2 | 12/2017 | Min et al. |
| 11,766,456 B2 | 9/2023 | Min et al. |
| 2003/0068306 A1 | 4/2003 | Dilber |
| 2004/0214783 A1 | 10/2004 | Terman |
| 2007/0048290 A1 | 3/2007 | Tsai |
| 2008/0138833 A1 | 6/2008 | Braun et al. |
| 2010/0144538 A1 | 6/2010 | Belouchi et al. |
| 2010/0178276 A1 | 7/2010 | Sadelain et al. |
| 2012/0045423 A1 | 2/2012 | Har-Noy |
| 2013/0011376 A1 | 1/2013 | Peled et al. |
| 2014/0023626 A1* | 1/2014 | Peled ............. A61K 35/17 435/375 |
| 2014/0050710 A1 | 2/2014 | Gonzalez et al. |
| 2014/0080148 A1 | 3/2014 | Spanholtz |
| 2015/0152387 A1 | 6/2015 | Lee et al. |
| 2017/0319621 A1 | 11/2017 | Min et al. |
| 2019/0037831 A1 | 2/2019 | Hwang et al. |
| 2019/0336533 A1 | 11/2019 | Hwang et al. |
| 2020/0108096 A1 | 4/2020 | Min et al. |
| 2021/0147803 A1 | 5/2021 | Hwang et al. |
| 2021/0179733 A1 | 6/2021 | Lee et al. |

(Continued)

FOREIGN PATENT DOCUMENTS

| CA | 2977472 | 9/2016 |
|---|---|---|
| CN | 103068973 | 4/2013 |

(Continued)

OTHER PUBLICATIONS

Min, Bokyung. Identification of NK cell costimulatory receptors for large-scale expansion of NK cells for adoptive immunotherapy in cancer patients. May 28, 2018. PHD Thesis (Year: 2018).*
Park et al., "CD4 T-cells transduced with CD80 and 4-1BBL mRNA induce long-term CD8 T-cell responses resulting in potent antitumor effects," Vaccine, Nov. 2014, 32: 6919-6926.
Cheng et al., "NK cell-based immunotherapy for malignant diseases," Cell. Mol. Immunol., May 2013, 10(3):230-252.
U.S. Appl. No. 18/455,003, filed Aug. 24, 2023, Min et al.
GenBank Accession No. NM_000594.3, "*Homo sapiens* tumor necrosis factor (TNF), mRNA," Sep. 30, 2018, 4 pages.

(Continued)

*Primary Examiner* — Maria G Leavitt
*Assistant Examiner* — Vyoma Shubham Tiwari
(74) *Attorney, Agent, or Firm* — Fish & Richardson P.C.

(57) ABSTRACT

The present invention relates to a method for culturing cord blood-derived natural killer cells using transformed T cells. The method of the present invention uses transformed T cells to culture natural killer cells and enables effective proliferation and production of natural killer cells from a small amount of seed cells. In addition, natural killer cells produced by the method of the present invention have improved cytotoxicity. Therefore, the method of the present invention is useful in commercializing natural killer cells for cell therapy. Furthermore, natural killer cells produced by the method of the present invention are useful for cell therapy.

11 Claims, 21 Drawing Sheets

Specification includes a Sequence Listing.

(56) References Cited

U.S. PATENT DOCUMENTS

| | | |
|---|---|---|
| 2021/0268025 A1 | 9/2021 | Min |
| 2024/0050478 A1 | 2/2024 | Min et al. |

FOREIGN PATENT DOCUMENTS

| | | |
|---|---|---|
| CN | 102112600 | 9/2014 |
| CN | 102911918 | 12/2014 |
| CN | 104204194 | 12/2014 |
| CN | 104321425 | 1/2015 |
| CN | 105602899 | 5/2016 |
| CN | 106222141 | 12/2016 |
| CN | 108300693 | 7/2018 |
| CN | 108300697 | 7/2018 |
| EP | 2856876 | 4/2015 |
| EP | 3633029 | 4/2020 |
| JP | 2004-501110 | 1/2004 |
| JP | 2008-544760 | 12/2008 |
| JP | 2010-501173 | 1/2010 |
| JP | 2010-523083 | 7/2010 |
| JP | 2011-529341 | 12/2011 |
| JP | 2012-521215 | 9/2012 |
| JP | 2013-006793 | 1/2013 |
| JP | 2013-027385 | 2/2013 |
| JP | 2013-071915 | 4/2013 |
| JP | 2015-502756 | 1/2015 |
| JP | 2015-513403 | 5/2015 |
| JP | 2018-520993 | 8/2015 |
| JP | 5840837 | 1/2016 |
| JP | 2017-525370 | 9/2017 |
| JP | 2018-501779 | 1/2018 |
| JP | 7039623 | 3/2022 |
| KR | 10-2008-0008060 | 1/2008 |
| KR | 10-2009-0121694 | 11/2009 |
| KR | 10-2010-0011586 | 2/2010 |
| KR | 10-2010-0012586 | 2/2010 |
| KR | 10-1035556 | 5/2011 |
| KR | 10-1133185 | 5/2011 |
| KR | 10-2011-0132618 | 12/2011 |
| KR | 10-2012 0091012 | 8/2012 |
| KR | 10-1298012 | 8/2013 |
| KR | 10-2014-0123503 | 10/2014 |
| KR | 10-1520534 | 5/2015 |
| KR | 10-2016-0063114 | 6/2016 |
| KR | 10-2016-0066837 | 6/2016 |
| KR | 10-1644984 | 8/2016 |
| KR | 10-1706524 | 2/2017 |
| WO | WO 97/05239 | 2/1997 |
| WO | WO 1997/032970 | 9/1997 |
| WO | WO 98/06822 | 2/1998 |
| WO | WO 2005/014637 | 2/2005 |
| WO | WO 2005/007116 | 12/2006 |
| WO | WO 2007/111677 | 10/2007 |
| WO | WO 2008/023874 | 2/2008 |
| WO | WO 2008/121420 | 10/2008 |
| WO | WO 2008/133845 | 11/2008 |
| WO | WO 2008/138214 | 11/2008 |
| WO | WO 2009/060865 | 5/2009 |
| WO | WO 2009/132192 | 10/2009 |
| WO | WO 2009/132283 | 10/2009 |
| WO | WO 2009/151183 | 12/2009 |
| WO | WO 2010/013947 | 5/2010 |
| WO | WO 2010/110734 | 9/2010 |
| WO | WO 2011/080740 | 7/2011 |
| WO | WO 2013/094988 | 6/2013 |
| WO | WO 2014/188680 | 11/2014 |
| WO | WO 2015/157386 | 10/2015 |
| WO | WO 2016/069993 | 5/2016 |
| WO | WO 2016/085248 | 6/2016 |
| WO | WO 2016/139463 | 9/2016 |
| WO | WO 2016/154585 | 9/2016 |
| WO | WO 2017/135631 | 8/2017 |
| WO | WO 2018/124766 | 7/2018 |
| WO | WO 2018/197859 | 11/2018 |
| WO | WO 2018/217064 | 11/2018 |
| WO | WO 2019/098682 | 5/2019 |
| WO | WO 2019/182392 | 9/2019 |
| WO | WO 2020/055040 | 3/2020 |
| WO | WO 2020/101361 | 5/2020 |
| WO | WO 2021/235894 | 11/2021 |
| WO | WO 2022/133056 | 6/2022 |
| WO | WO 2022/133057 | 6/2022 |
| WO | WO 2022/133061 | 6/2022 |
| WO | WO 2022/216144 | 10/2022 |
| WO | WO 2022/216811 | 10/2022 |
| WO | WO 2022/216813 | 10/2022 |
| WO | WO 2022/216815 | 10/2022 |
| WO | WO 2022/216826 | 10/2022 |
| WO | WO 2022/216831 | 10/2022 |
| WO | WO 2022/216837 | 10/2022 |
| WO | WO 2023/080895 | 5/2023 |
| WO | WO 2023/081317 | 5/2023 |
| WO | WO 2024/040135 | 2/2024 |
| WO | WO 2024/119126 | 6/2024 |

OTHER PUBLICATIONS

GenBank Accession No. NM_003811.3, "*Homo sapiens* TNF superfamily member 9 (TNFSF9), mRNA," May 21, 2018, 4 pages.

GenPept Accession No. NP_003317, "tumor necrosis factor ligand superfamily member 4 isoform 1 [*Homo sapiens*]," Oct. 21, 2018, 3 pages.

GenPept Accession No. PDB:2OQP_A, "Chain A, Interleukin-21," May 17, 2018, 2 pages.

Mock et al., "Automated manufacturing of chimeric antigen receptor T cells for adoptive immunology using CliniMACs Prodigy," Cytotherapy, Aug. 2016, 18(8):1002-1011.

Office Action in Chinese Application No. 201980075094.X, dated Dec. 5, 2023, 17 pages (with English Translation).

Squiban et al., "Creation of a Human T-ALL Cell Line Online Database Human T-ALL cell line database," Leuk. Lymphoma, Nov. 2017, 58(11):2728-2730.

KR Office Action in Korean Appln. No. 10-2019-0145068, dated Jul. 22, 2021, 11 pages (with English translation).

Li et al., "Expansion of NK cells from PBMCs using immobilized 4-1BBL and interleukin-21", International Journal of Oncology, 2015, 47:335-342.

Hassell et al., "Adaptation to non-ammoniagenic medium and selective substrate feeding lead to enhanced yields in animal cell cultures," Journal of Cell Science, Jul. 1990, 96(3):501-508.

JP Office Action in Japanese Appln. No. 2021-526674, dated May 10, 2022, 9 pages (with English translation).

GenBank Accession No. LN874322.1, "TPA_inf: *Homo sapiens* mRNA for tumor necrosis factor ligand 5A (TNLG5A gene)," dated Jun. 8, 2016, 2 pages.

Carswell et al., "Culture of Human T Cells in Stirred Bioreactors for Cellular Immunotherapy Applications: Shear, Proliferation, and the IL-2 Receptor," Biotechnology & Bioengineering, May 5, 2000, 68(3):328-338.

U.S. Appl. No. 14/367,813 (Corresponds to U.S. Pat. No. 9,834,753 cited in an IDS on Dec. 10, 2021), filed Jun. 20, 2014, Min et al.

U.S. Appl. No. 16/702,978, filed Dec. 4, 2019, Min et al.

U.S. Appl. No. 15/527,752 (Corresponds to US 2017/0319621 cited in an IDS on Aug. 2, 2022), filed May 18, 2017, Min et al.

U.S. Appl. No. 17/220,865 (Corresponds to US 2021/0268025 cited in an IDS on Oct. 6, 2021), filed Apr. 1, 2021, Min et al.

U.S. Appl. No. 16/613,601 (Corresponds to US 2020/0108096 cited in an IDS on Mar. 11, 2022), filed Nov. 14, 2019, Min et al.

U.S. Appl. No. 17/040,661 (Corresponds to US 2021/0147803 cited in an IDS on Mar. 11, 2022), filed Jan. 14, 2021, Hwang et al.

Granzin et al., "Fully automated expansion and activation of clinical-grade natural killer cells for adoptive immunotherapy," Cytotherapy, May 2015, 17(5):621-632.

Granzin et al., "Highly efficient IL-21 and feeder cell-driven ex vivo expansion of human NK cells with therapeutic activity in a xenograft mouse model of melanoma," OncoImmunology, 2016, 5(9):e1219007.

Granzin, "Highly Efficient Activation and Expansion of Natural Killer Cells For Clinical Use in Cancer Immunotherapy, "Dissertation for the Degree of Doctor of Natural Sciences, Combined Faculties for the Natural Sciences and for Mathematics of the

(56) References Cited

OTHER PUBLICATIONS

Ruperto-Carola University of Heidelberg, Germany, Apr. 25, 2016, 136 pages.
Peirson et al., "Production of Human Natural Killer Cells for Adoptive Immunotherapy Using a Computer-Controlled Stirred-Tank Bioreactor," Journal of Hematotherapy, 1996, 5(5):475-483.
Min et al., "Harnessing novel engineered feeder cells expressing activating molecules for optimal expansion of NK cells with potent antitumor activity," Cellular & Molecular Immunology, 2022, 19(2):296-298 (Supplemental Figure S4 only).
Valle et al., "Heterogeneous CD3 Expression Levels in Differing T Cell Subsets Correlate with the In Vivo Anti-CD3-Mediated T Cell Modulation," The Journal of Immunology, 2015, 194:2117-2127.
Extended European Search Report in Patent Appln. No. 19885404. 4, dated Jul. 29, 2022, 8 pages.
Min et al., "Harnessing novel engineered feeder cells expressing activating molecules for optimal expansion of NK cells with potent antitumor activity," Cellular & Molecular Immunology, Sep. 27, 2021, 19(2):296-298.
Min et al., "Optimization of Large-Scale Expansion and Cryopreservation of Human Natural Killer Cells for Anti-Tumor Therapy," Immune Network, Jan. 1, 20118, 18(4):e31, 13 pages.
Ando et al., "Extensive generation of human cord blood CD34 stem cells from Lin 2CD34 cells in a long-term in vitro system" Exp. Hematol., 2000 28:690-9.
Bae et al., "Development of NK cell expansion methods using feeder cells from human myelogenous leukemia cell line," Blood Research, Sep. 2014, 49(3):154-61.
Baek et al., "Ex Vivo Expansion of Natural Killer Cells Using Cryopreserved Irradiated Feeder Cells," Anticancer Res., Jan. 2013, 33:2011-2020.
Berg et al., "Clinical Grade Ex Vivo-Expanded Human Natural Killer Cells Upregulate Activating Receptors and Death Receptor Ligands and Have Enhanced Cytolytic Activity against Tumor Cells," Cytotherapy, 2009, 11(3):41-355.
Boissel et al., "Umbilical Cord Mesenchymal Stem Cells Increase Expansion of Cord Blood Natural Killer Cells," Biology of Blood and Marrow Transplantation, Sep. 2008, 14(9):1031-8.
Byers "What Can Randomized Controlled Trials Tell US About Nutrition and Cancer Prevention?," Cancer Journal, 1999, 49(6):353-61.
Carlens et al., "A New Method for In Vitro Expansion of Cytotoxic Human CD3-CD56+ Natural Killer Cells, " Human Immunology, Oct. 2001, 62(10):1092-8.
Castriconi et al., "Human NK cell infusions prolong survival of metastatic human neuroblastoma-bearing NOD/scid mice" Cancer Immunol. Immunother., Nov. 2007, 56(11):1733-42.
Childs and Berg, "Bringing natural killer cells to the clinic: ex vivo manipulation," Hematology Am. Soc. Hematol. Educ. Program, 2013. 2013(1):234-46.
Condiotti et al., "Ex vivo expansion of CD56+ cytotoxic cells from human umbilical cord blood," Experimental Hematol., 2001, 29(1):104-13.
Dahlberg et al., "Natural Killer Cell-Based Therapies Targeting Cancer: Possible Strategies to Gain and Sustain Anti-Tumor Activity," Front. Immunol., 2015, 6:1-19).
Denman et al., "Membrane-Bound IL-21 Promotes Sustained Ex Vivo Proliferation of Human Natural Killer Cell" PloSONE, 2012, 7(1):e30264.
Dermer, "Another Anniversary for the War on Cancerm," Bio/Technology, 1994, 12:320.
Dewan et al., "Role of natural killer cells in hormone-independent rapid tumor formation and spontaneous metastasis of breast cancer cells in vivo" Breast Cancer Res. Treatment, 2007, 104(3):267-75.
Dunne et al., "Selective Expansion and Partial Activation of Human NK Cells and NK Receptor-Positive T Cells by IL-2 and IL-15," J. Immunol., 2001167(6):3129-38.
Edwards et al., "The Remarkable Flexibility of the Human Antibody Repertoire; Isolation of Over One Thousand Different Antibodies to a Single Protein, BLyS," JMB, 2003, 334:103-18.

Freshney, "Culture of Animal Cells, A Manual of Basic Technique," Alan R. Liss, Inc., 1983, 1-4.
Frias et al., "Generation of functional natural killer and dendritic cells in a human stromal-based serum-free culture system designed for cord blood expansion" Experimental Hematology, 2008, 36(1):61-8.
Fujisaki et al., "Expansion of Highly Cytotoxic Human Natural Killer Cells for Cancer Cell Therapy," Cancer Res., May 1, 2009,69(9):4010-7.
GenBank Accesion No. CAA56284.1, "OX 40 ligand/ gp 34 [*Homo sapiens*]", dated Oct. 7, 2008, 2 pages.
GenBank Accession No. LN874322.1, "TPA_inf: *Homo sapiens* mRNA for tumor necrosis factor ligand 5A (TNLG5A gene)," dated Nov. 28, 2019, 2 pages.
GenBank Accestion No. NM_001768.7, "*Homo sapiens* CD8a molecule (CD8A), transcript variant 1, mRNA" dated Feb. 27, 2020, 4 pages.
GenBank Accession No. NM_003326.5, "*Homo sapiens* TNF superfamily member 4 (TNFSF4), transcript variant 1, mRNA" dated Nov. 23, 2018, 4 pages.
GenBank Accession No. NM_003811.4, "*Homo sapiens* TNF superfamily member 9 (TNFSF9), mRNA" dated Nov. 22, 2018, 4 pages.
GenBank Accestion No. NM_021803.3, "*Homo sapiens* interleukin 21 (IL21), transcript variant 1, mRNA," dated Jun. 17, 2018, 3 pages.
Goel et al., "Plasticity within the Antigen-Combining Site May Manifest as Molecular Mimicryin the Hurnoral Immune Response," J. Immunol., 2004, 173:7358-67.
Gong et al., "Ex vivo expansion of natural killer cells with high cytotoxicity by K562 cells modified to co express major histocompatibility complex class I chain-related protein A, 4-1 BB ligand, and interleukin-15," Tissue Antigens, 2010, 76(6):467-75.
Goodier et al., "Lipopolysaccharide Stimulates the Proliferation of Human CD56+CD3-NK Cells: A Regulatory Role of Monocytes and IL-10," J. Immunology, 2000, 165(1):139-47.
Holmes et al., "A Human NK Cell Activation/Inhibition Threshold Allows Small Changes in the Target Cell Surgace Phenotype To Dramatically Alter Susceptibility to NK Cells," J. Immunol., 2011, 186:1538-45.
iwai-chem.co.jp [online] "DataSheet: CellGro/CellGenix GMP Serum-free StemCell GrowthMedium (SCGM) Xeno-free", May 16, 2011, via Internet Archive: Wayback Machine URL <https://web.archive.org/web/20140124200115/http://www.iwai-chem.co.jp/products/cellgenix/20802-0500.pdf>, retrieved on Jul. 23, 2021, URL<http://www.iwai-chem.co.jp/products/cellgenix/20802-0500.pdf>, 1 page.
Kelly et al., "Memory CD4+ T Cells Are Required for Optimal NK Cell Effector Functions against the Opportunistic Fungal Pathogen Pneumocystis murina", J. Immunology, 2013, 190:285-95.
Keridiles et al., "T cell regulation of natural killer cells", J. Experimental Medicine, Jun. 2013, 210(6):1065-8.
Khan and Salunke, " Adjustable Locks and Flexible Keys: Plasticity of Epitope-Paratope Interactions in Germline Antibodies," J. Immunol., 2014, 192(11):5398-405.
Kim et al., "Ex vivo activation and expansion of natural killer cells from patients with advanced cancer with feeder cells from healthy volunteers", Cytotherapy, 2013, 15:231-41.
Koehl et al., "IL-2 activated NK cell immunotherapy of three children after haploidentical stem cell transplantation," Blood Cells Molecules & Disease, November-Dec. 2004, 33(3):261-6.
KR Office Action in Korean Appln. No. 10-2019-0145068, dated Apr. 19, 2021, 12 pages (with English translation).
Lim et al., "Ex Vivo Expansion of Highly Cytotoxic Human NK Cells by Cocultivation with Irradiated Tumor Cells for Adoptive Immunotherapy," Cancer Res., Apr. 15, 2013, 73(8):2598-607.
Lim et al., "GMP-Compliant, Large-Scale Expanded Allogeneic Natural Killer Cells Have Potent Cytolytic Activity against Cancer Cells In Vitro and In Vivo," PlosOne, Jan. 2013, 8(1):1-9.
Lloyd et al., "Modelling the human immune response: performance of a human antibody repertoire against a 10 broad panel of therapeutically relevant antigens," Protein Engineering, Eng. Design & Selection, 2009, 22(3):159-68.
Miller et al., "Role of monocytes in the expansion of human activated natural killer cells, " Blood, Nov. 1992, 80(9):2221-9.

(56) References Cited

OTHER PUBLICATIONS

Min, "Identification of NK cell costimulatory receptors for large-scale expansion of NK cells for adoptive immunotherapy in cancer patients ," Thesis for the degree of Doctor ,2018, http://library.kaist.ac.kr/search/detail/view.do?bibCtrlNo=827940&flag-dissertation.
Mingari et al., "In Vitro Proliferation and Cloning of CD3-CD16+ Cells from Human Thymocyte Precursors", J. Exp. Med., Jul. 1991, 174:21-6.
Miyahira, "Types of Immune Cells Present in Human PBMC," Sanguine Bio Researcher Blog, Nov. 22, 2012, 3 pages.
Morris et al., "A high-efficiency system of natural killer cell cloning," Journal of Immunological Methods,2005, 307(1-2):24-33.
North et al., "Tumor-Primed Human Natural Killer Cells Lyse NK-Resistant Tumor Targets: Evidence of a Two-Stage Process in Resting NK Cell Activation," J. Immunology, 2007, 178(1):85-94.
PCT International Preliminary Report on Patentability in International Appln. No. PCT/KR2019/015469, dated May 18, 2021, 9 pages.
PCT International Search Report and Written Opinion International Appln. No. PCT/KR2019/015469, dated Feb. 25, 2020, 15 pages.
Perez et al., "A potential role for hydrocortisone in the positive regulation of IL-15-activated NK-cell proliferation and survival," Blood, Jul. 2005, 106(1):158-66.
Poggi et al., "Extrathymic differentiation of T lymphocytes and natural killer cells from human embryonic liver precursors", Proc. Natl. Acad. Sci. USA, May 1993, 90:4465-9.
Poosarla et al., "Computational De Novo Design of Antibodies Binding to a Peptide With High Affinity," Biotechn. Bioeng., 2017, 114(6): 1331-42.
Siegler et al., "Good manufacturing practice-compliant cell sorting and large-scale expansion of single KIR-positive alloreactive human natural killer cells for multiple infusions to leukemia patients," Cytotherapy, 2010, 12:750-63.
Sigmaaldrich.com, "Sigma-Aldrich H9", retrieved on Nov. 15, 2019, retrieved from URL <https://www.sigmaaldrich.com/catalog/productUsigma/cb_85050301?lang=en&region=US&cm_sp=Insite-_-prodRecCold_xviews-_-prodRecCold10-1>, 3 pages.
Torres and Casadevall, "The immunoglobulin constant region contributes to affinity and specificity," Trend. Immunol., Jan. 2008, 29(2): 91-7.
Vansdol et al., "Generation of Functional CD56+ Natural Killer (NK) Cells from Ex Vivo Expanded Human Cord Blood (CB) Hematopoietic Stem Cells", Blood, 2000, Abstract#424, 96(11):128b.
Vitale et al., "Effect of Tumor Cells and Tumor Microenvironment on NK-cell Function" Euro. J. Immunol., 2014, 44:1582-92.
Www.thermofisher.com [online] "CTS (TM) AIM V (R) Medium", Aug. 24, 2015, retrieved from URL<http://www.thermofisher.com/order/catalog/product/0870112BK?ICID=search-product>, 4 pages.
Xiao-Hong et al., "Ex vivo expansion of highly purified NK cells from human peripheral blood",Zhongguo shi yan xue ye xue za zhi.., Apr. 2007, 15(2):373-7.
Zips et al., "New AntiCancer Agents: In Vitro and In Vivo Evaluation" In vivo, 2005, 19:1-8.
AU Office Action in Australian Appln. No. 2019381526, dated Oct. 6, 2022, 5 pages.
Ahn et al., "Irradiated and Activated Autologous PBMCs Induce Expansion of Highly Cytotoxic Human NK Cells In Vitro," Journal of Immunotherapy, Sep. 2013, 36(7):373-381.
Almishri et al., "TNFα augments cytokine-induced NK Cell IFNγ production through TNFR2," Journal of Innate Immunity, 2016, 8(6):617-629.
Carson et al., "A potential role for interleukin-15 in the regulation of human natural killer cell survival.," The Journal of Clinical Investigation, Mar. 1, 1997, 99(5):937-943.
Choi et al., "Donor-Derived Natural Killer Cells Infused after Human Leukocyte Antigen-Haploidentical Hematopoietic Cell Transplantation: A Dose-Escalation Study," Biology of Blood and Marrow Transplantation, 2014, 20(5):696-704.
Croft, "Control of immunity by the TNFR-related molecule OX40 (CD134)," Annual Review of Immunology, 2010, 28(1):57-78.
Granzin et al., "Shaping of Natural Killer Cell Antitumor Activity by Ex Vivo Cultivation," Frontiers in Immunology, Apr. 26, 2017, 8:458, 18 pages.
Lee et al., "Expansion of cytotoxic natural killer cells using irradiated autologous peripheral blood mononuclear cells and anti-CD16 antibody," Scientific Reports, Sep. 11, 2017, 7(1):1-13.
Mason et al., "Regulation of NK cells through the 80-kDa TNFR (CD120b)," Journal of Leukocyte Biology, Aug. 1, 1995, 58(2):249-255.
MY Office Action in Malaysian Appln. No. PI202102566, dated Aug. 11, 2022, 3 pages.
Parkhurst et al., "Adoptive Transfer of Autologous Natural Killer Cells Leads to High Levels of Circulating Natural Killer Cells but Does Not Mediate Tumor Regression," Clinical Cancer Research, Oct. 1, 2011, 17(19):6287-6297.
Parrish-Novak et al., "Interleukin 21 and its receptor are involved in NK cell expansion and regulation of lymphocyte function," Nature, Nov. 2, 2000, 408(6808):57-63.
Parrish-Novak et al., "Interleukin-21 and the IL-21 receptor: novel effectors of NK and T cell responses," Journal of Leukocyte Biology, Nov. 1, 2002, 72(5):856-863.
Sakamoto et al., "Phase I clinical trial of autologous NK cell therapy using novel expansion method in patients with advanced digestive cancer," Journal of Translational Medicine, Aug. 25, 2015, 13:277, 13 pages.
Shuford et al., "4-1BB Costimulatory Signals Preferentially Induce CD8+ T Cell Proliferation and Lead to the Amplification In Vivo of Cytotoxic T Cell Responses," The Journal of Experimental Medicine, Jul. 7, 1997, 186(1):47-55.
Turaj et al., "Augmentation of CD 134 (OX40)-dependent NK anti-tumour activity is dependent on antibody cross-linking," Scientific Reports, Feb. 2018, 8(1):1-11.
Wendt et al., "Interleukin-21 differentially affects human natural killer cell subsets," Immunology, Dec. 2007, 122(4):486-495.
Wilcox et al., "Signaling through NK cell-associated CD137 promotes both helper function for CD8+ cytolytic T cells and responsiveness to IL-2 but not cytolytic activity," The Journal of Immunology, Oct. 15, 2002, 169(8):4230-4236.
Willoughby et al., "OX40: Structure and function—What questions remain?," Molecular Immunology, Mar. 2017, 83:13-22.
Xu et al., "Essential role of the TNF-TNFR2 cognate interaction in mouse dendritic cell-natural killer cell crosstalk," Blood, Apr. 15, 2007, 109(8):3333-3341.
Yang et al., "Phase I Study of Random Healthy Donor-Derived Allogeneic Natural Killer Cell Therapy in Patients with Malignant Lymphoma or Advanced Solid Tumors," Cancer Immunology Research, Mar. 1, 2016, 4(3):215-224.
Kim et al., "Engineering Conferences International ECI Digital Archives Scale-up study for ex-vivo expansion of allogeneic natural killer cells in stirred-tank bioreactor, Hyuang Jin nam Sang Hyun Lee Recommended Citation," Advancing Manufacture of Cell and Gene Therapies VI, Jan. 2019, 3 pages.
Spanholtz et al., "Clinical-Grade Generation of Active NK Cells from Cord Blood Hematopoietic Progenitor Cells for Immunotherapy Using a Closed-System Culture Process," PLoS One, Jun. 16, 2011, 6(6):1-11.
Office Action in Philippine Application No. 1/2021/550950, mailed on Oct. 21, 2024, 6 pages.
Communication pursuant to Article 94(3) EPC in European Appln. No. 19885404.4, mailed on Dec. 9, 2024, 4 pages.
Office Action in Canadian Application No. 3,120,085, dated Jan. 8, 2025, 4 pages.
Office Action in Chinese Application No. 201980075094.X, dated Jul. 12, 2024, 9 pages (with English Translation).
Office Action in Israeli Application No. 283176, dated Feb. 12, 2025, 3 pages.

* cited by examiner

[Fig. 1]
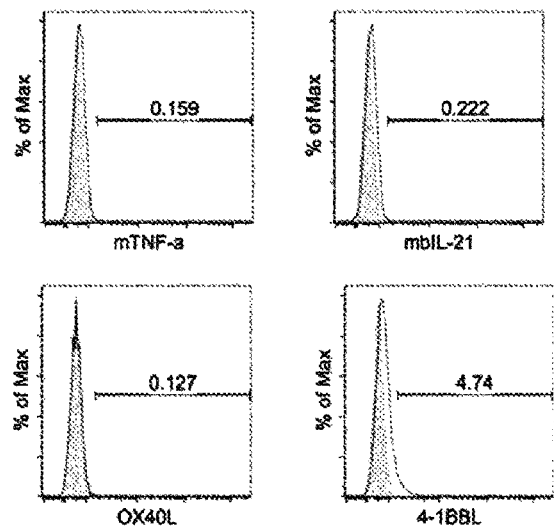
[Fig. 1b]
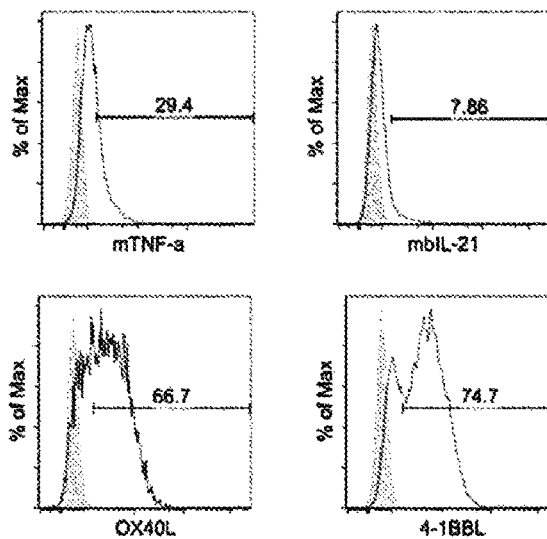

[Fig. 1c]
**Hut78 feeder cells
Double gene transduction**
(i) mTNF-α/OX40L
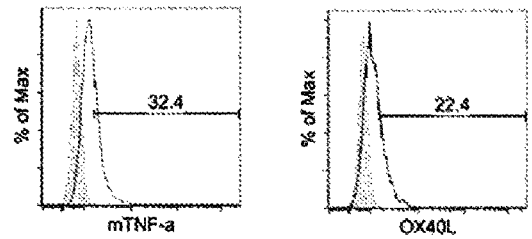
(ii) mTNF-α /4-1BBL
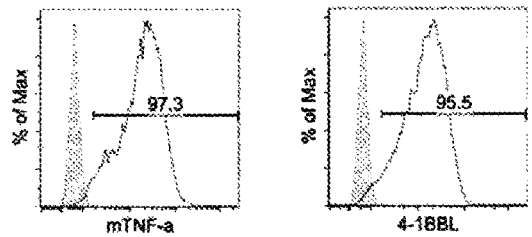
[Fig. 1d]
**Hut78 feeder cells
Double gene transduction**
(i) mbIL-21/OX40L
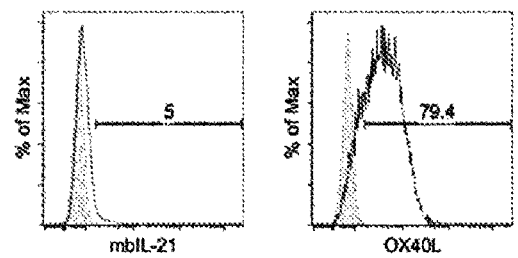
(ii) mbIL-21/4-1BBL
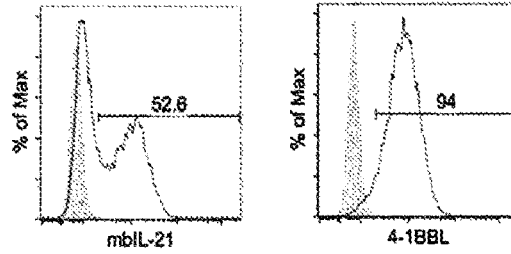

[Fig. 1e]
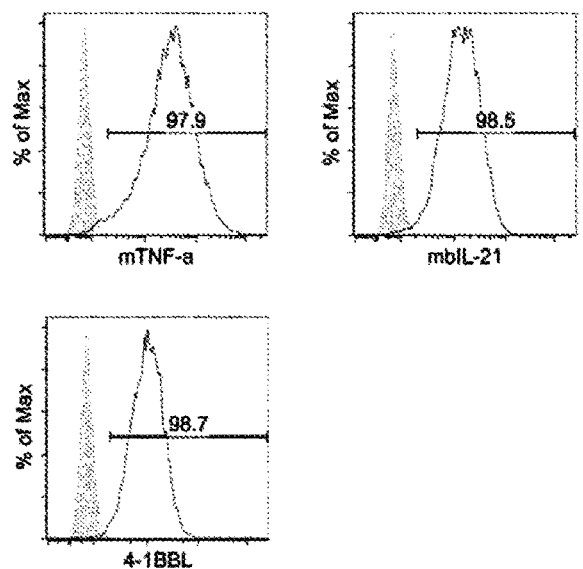
[Fig. 1f]
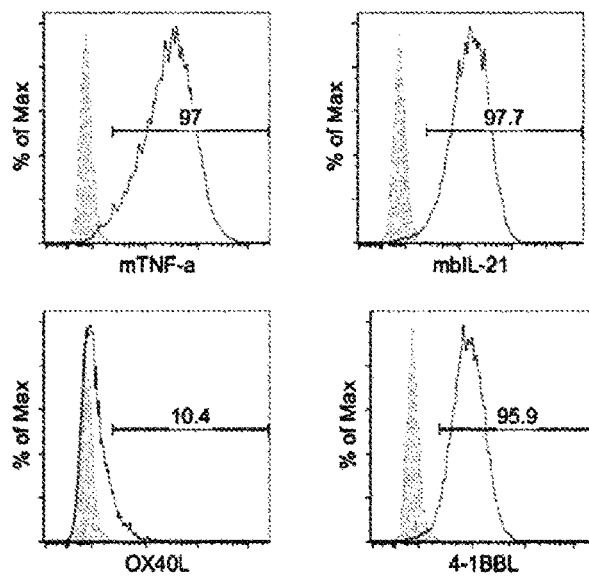

[Fig. 2a]
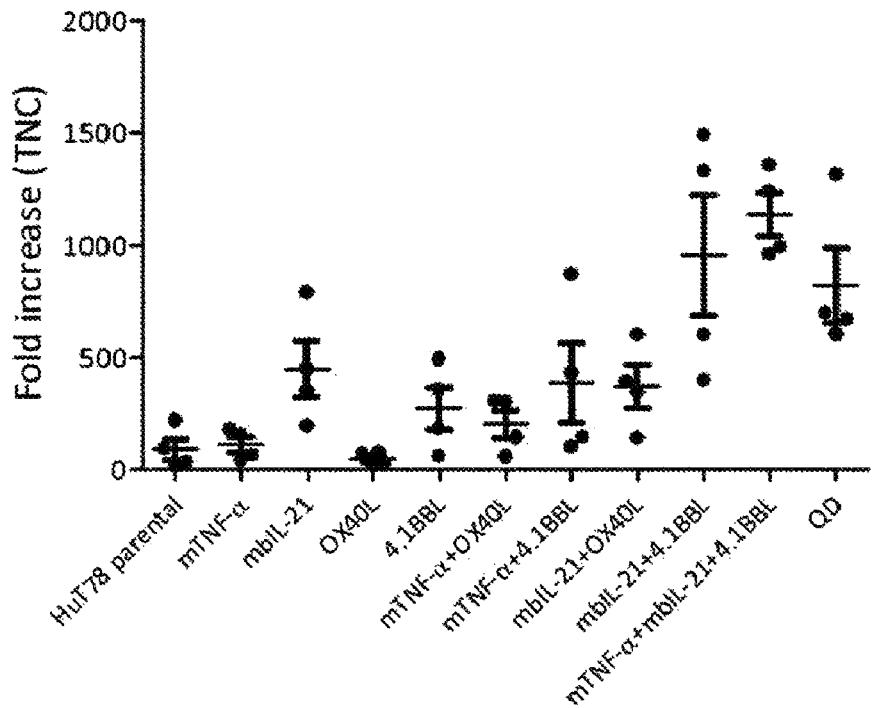
[Fig. 2b]
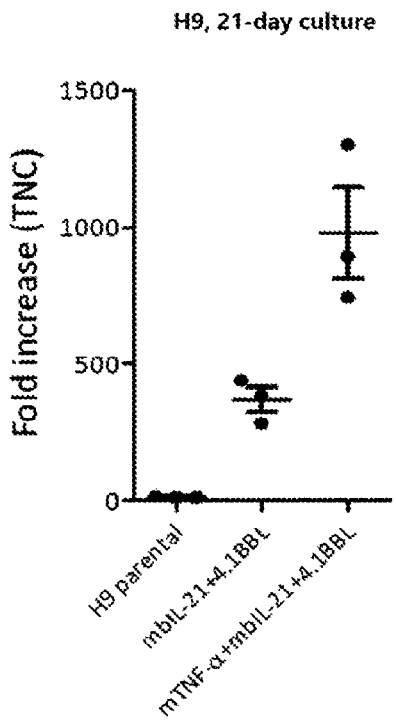

[Fig. 2c]
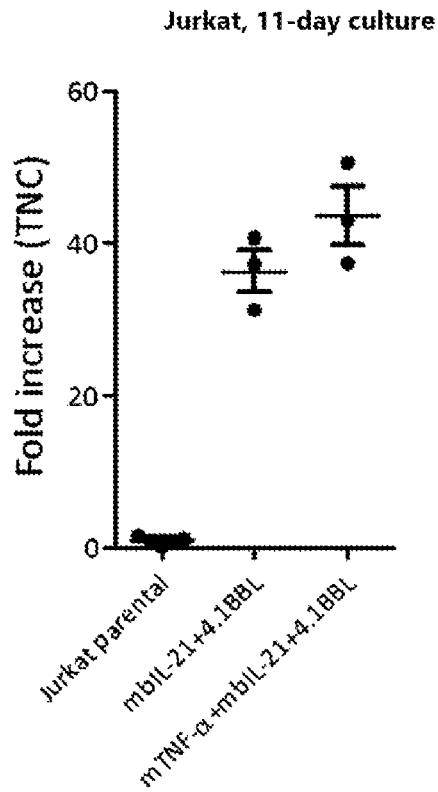
[Fig. 2d]
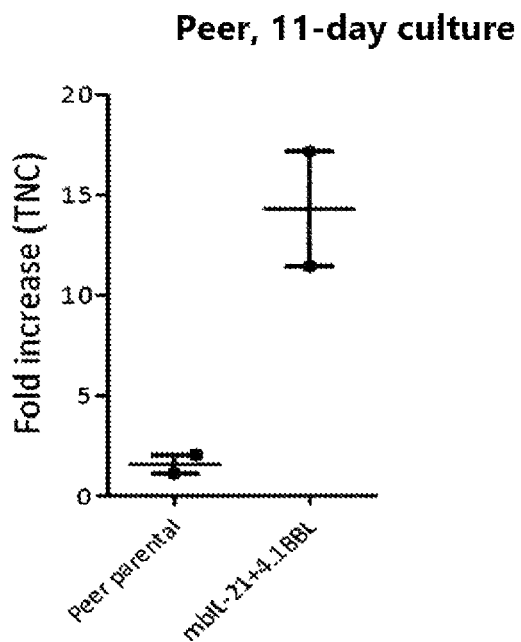

[Fig. 2e]
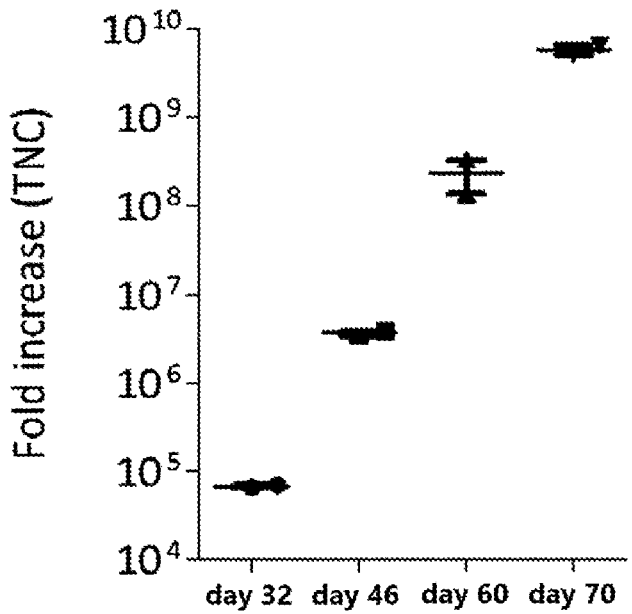
[Fig. 3a]
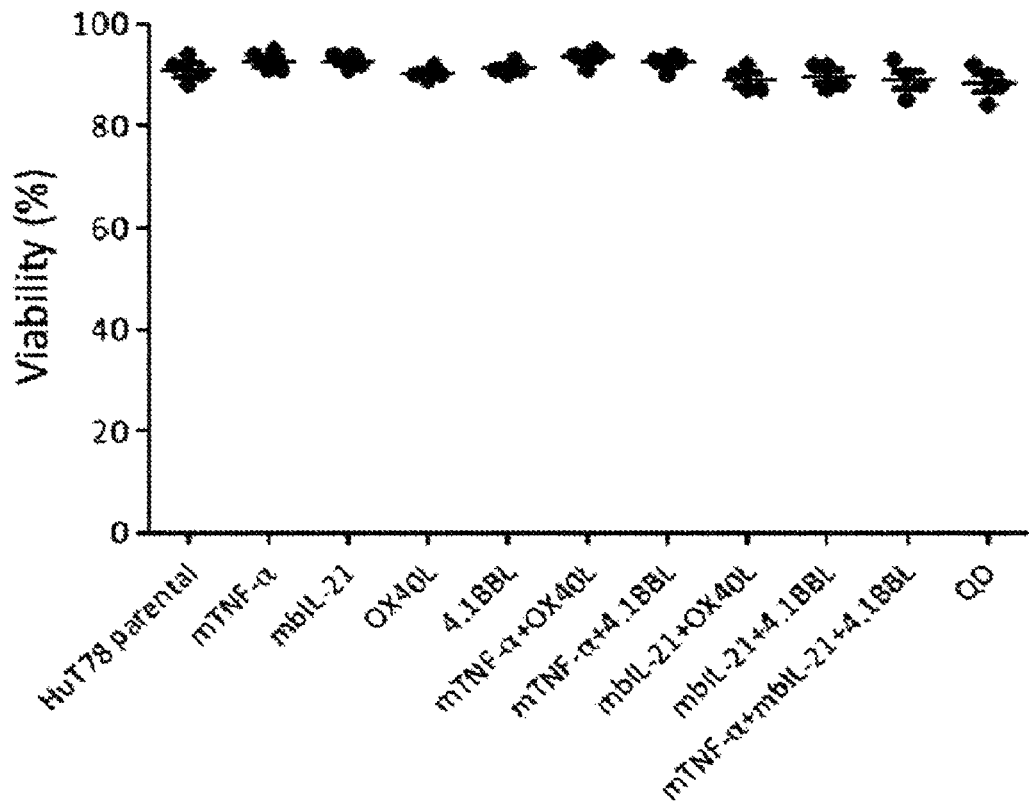

[Fig. 3b]
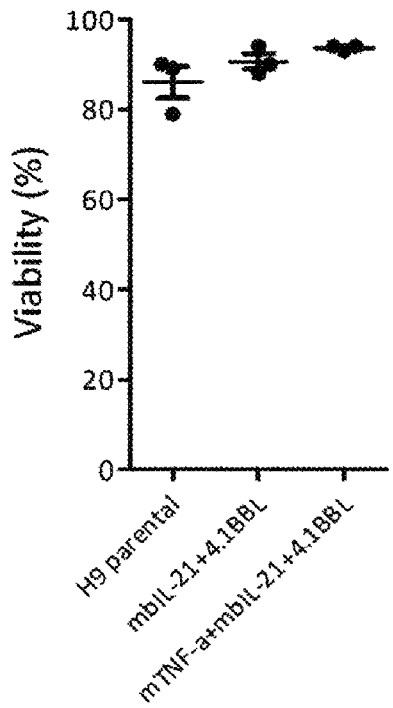
[Fig. 3c]
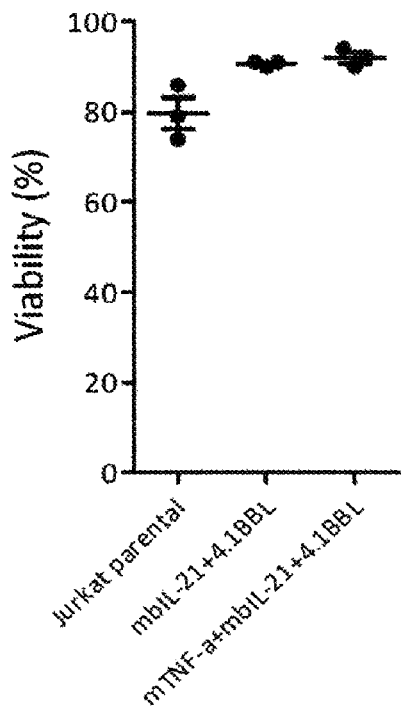

[Fig. 3d]
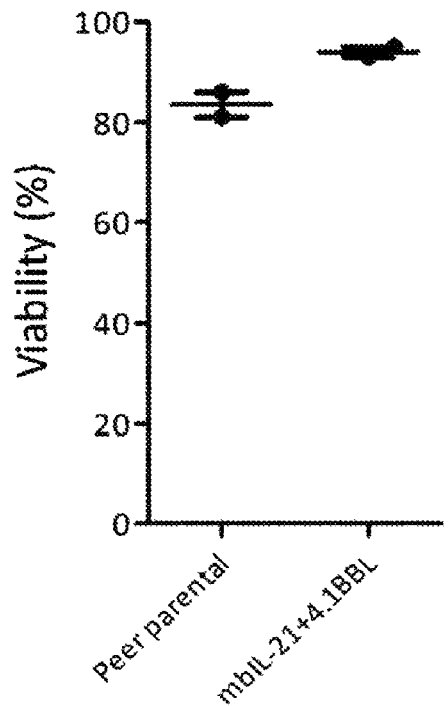
[Fig. 3e]
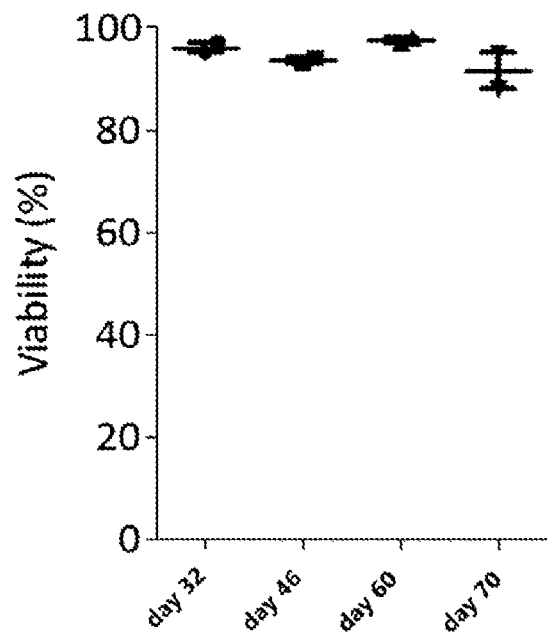

[Fig. 4a]
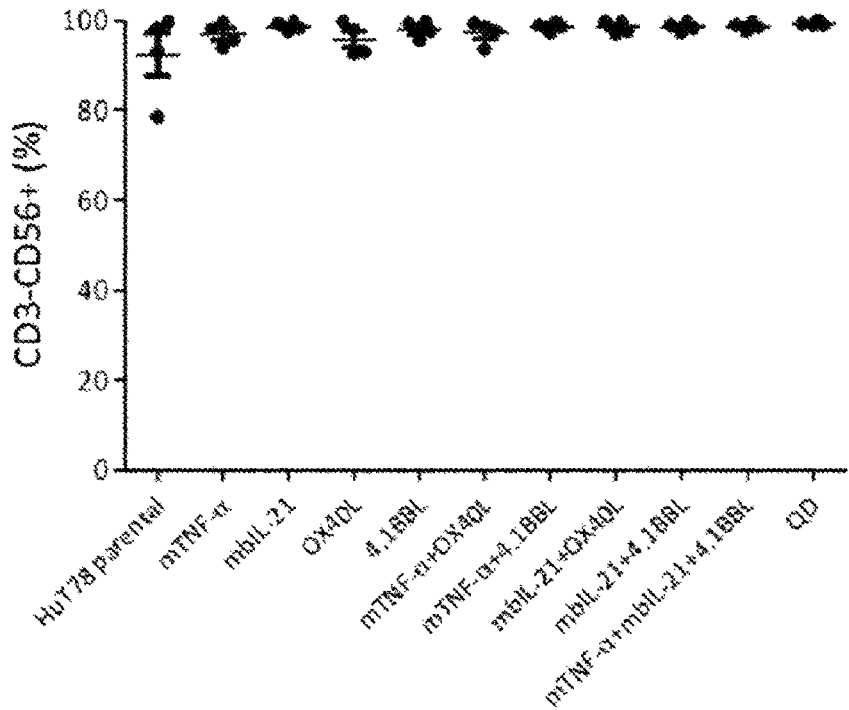
[Fig. 4b]
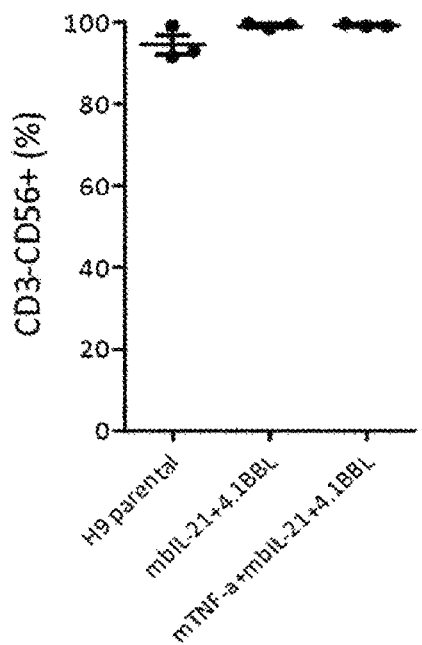

[Fig. 4c]
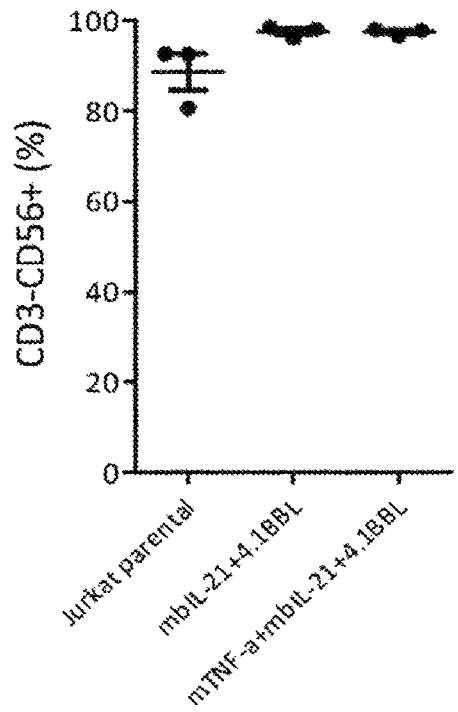
[Fig. 4d]
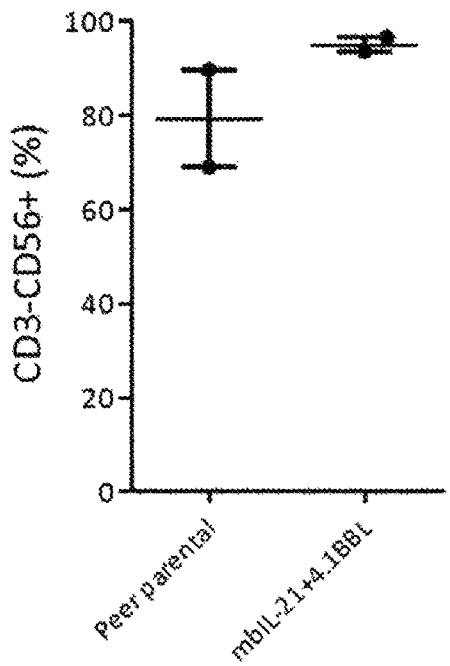

[Fig. 4e]
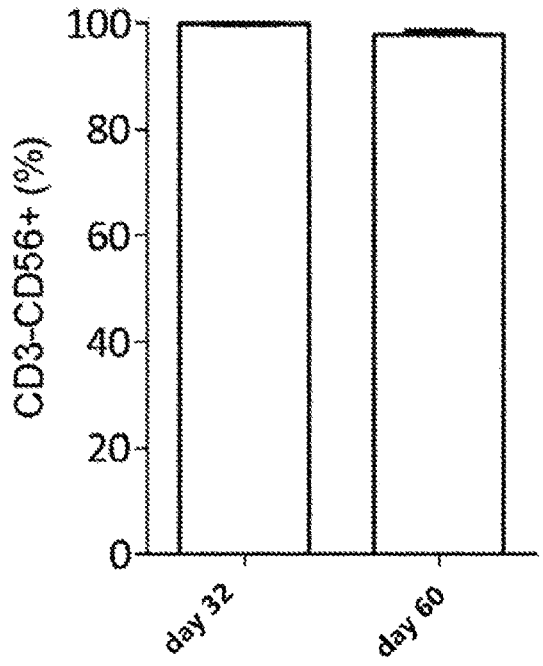
[Fig. 5a]
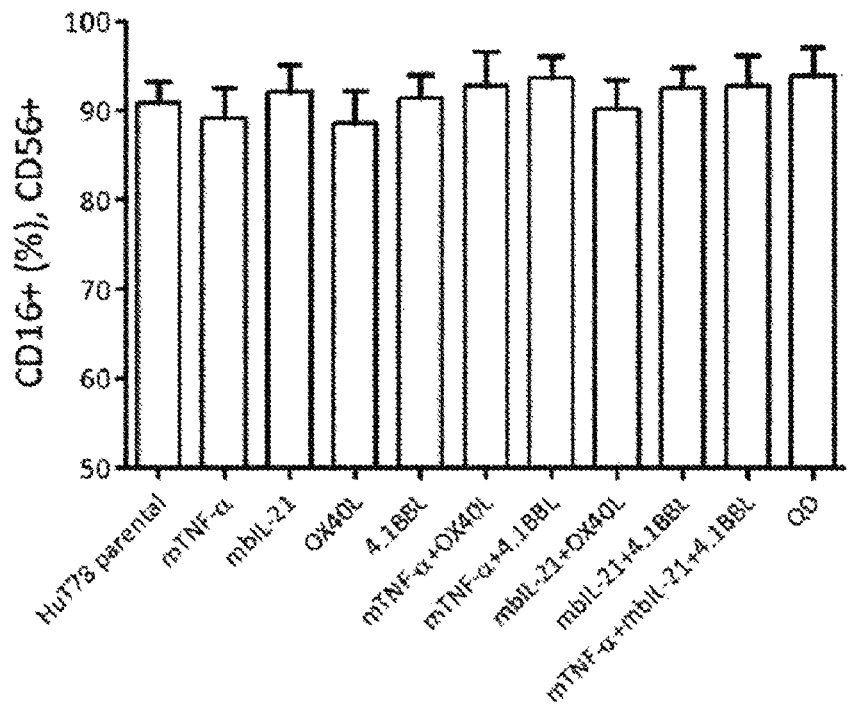

[Fig. 5b]
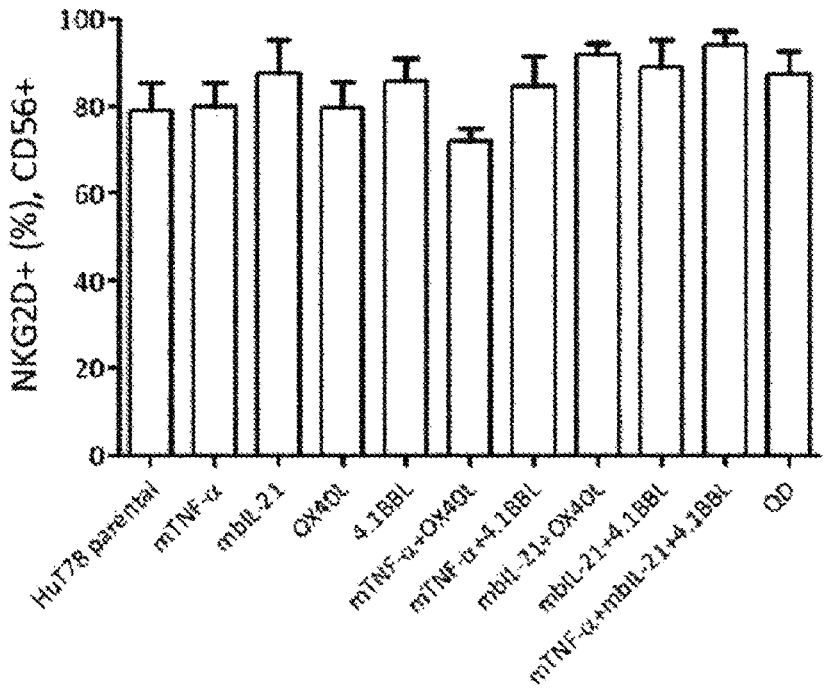
[Fig. 5c]
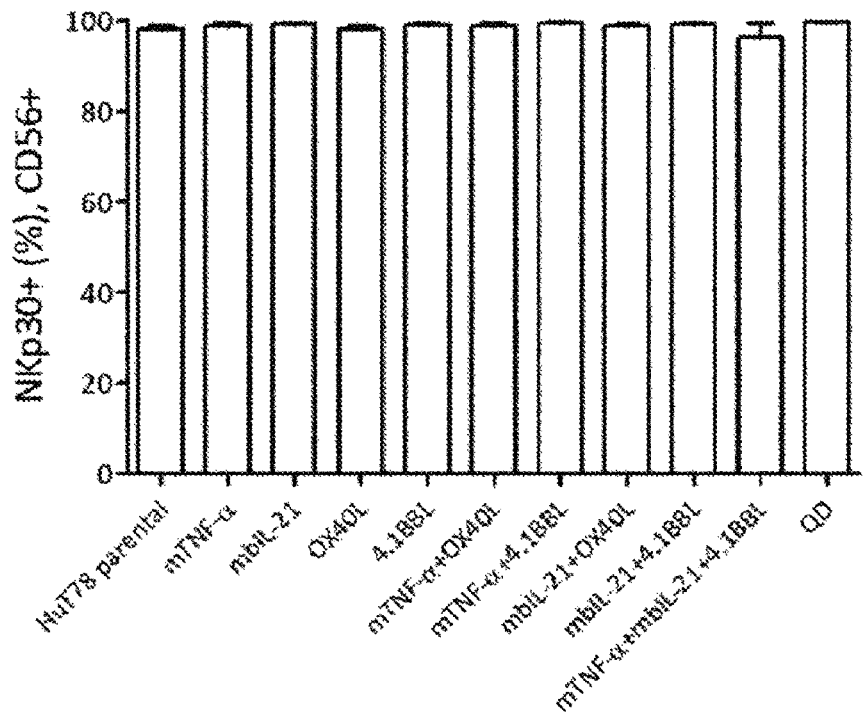

[Fig. 5d]
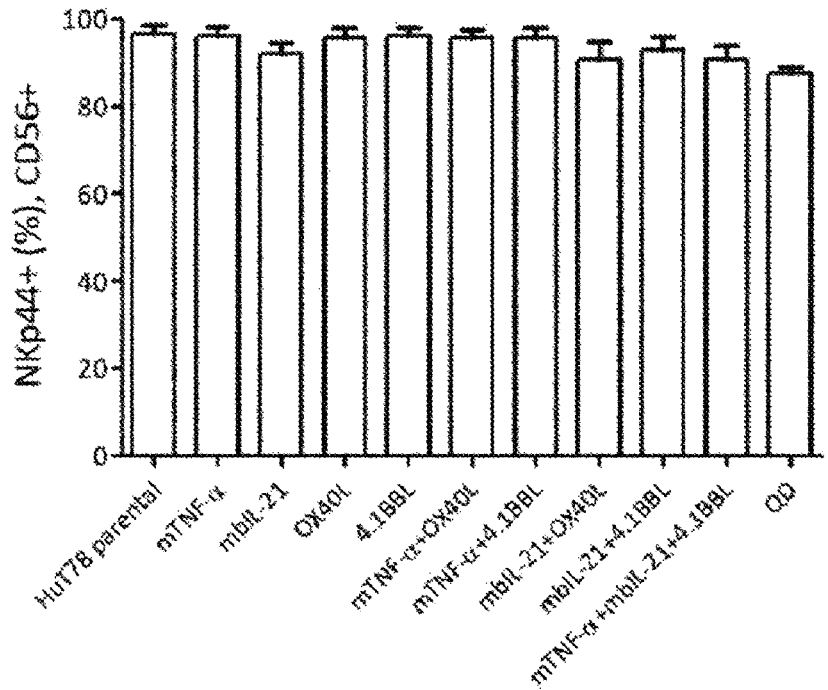
[Fig. 5e]
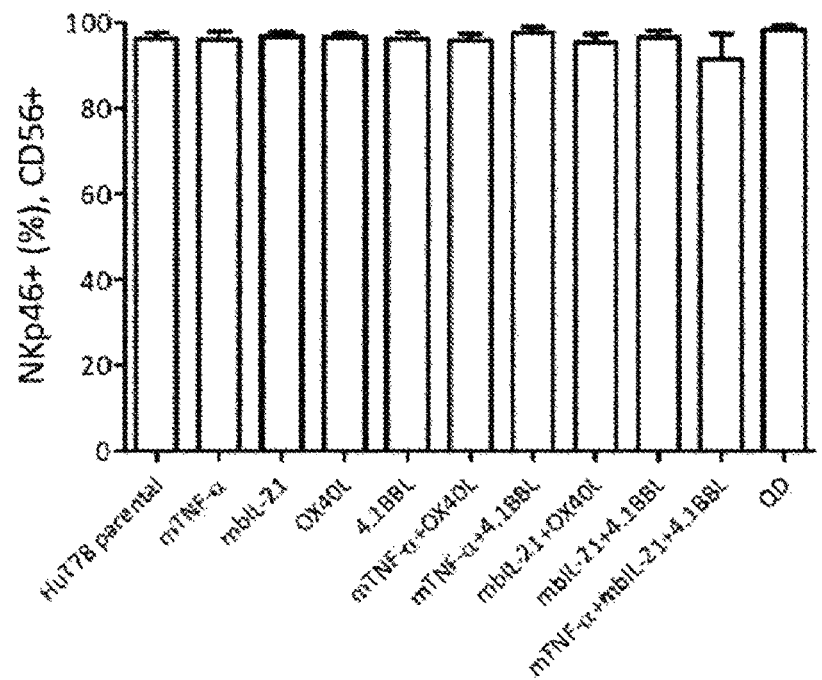

[Fig. 5f]
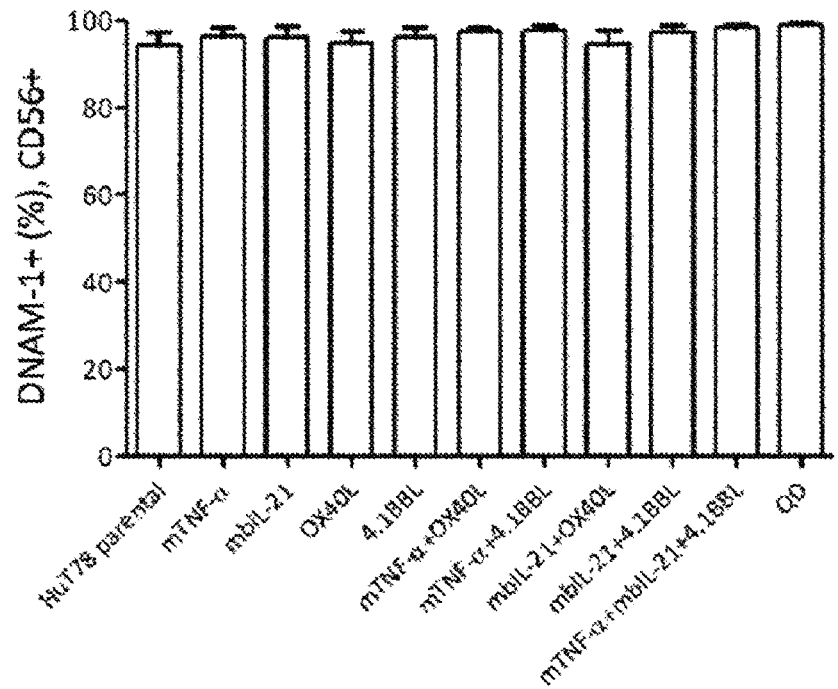
[Fig. 5g]
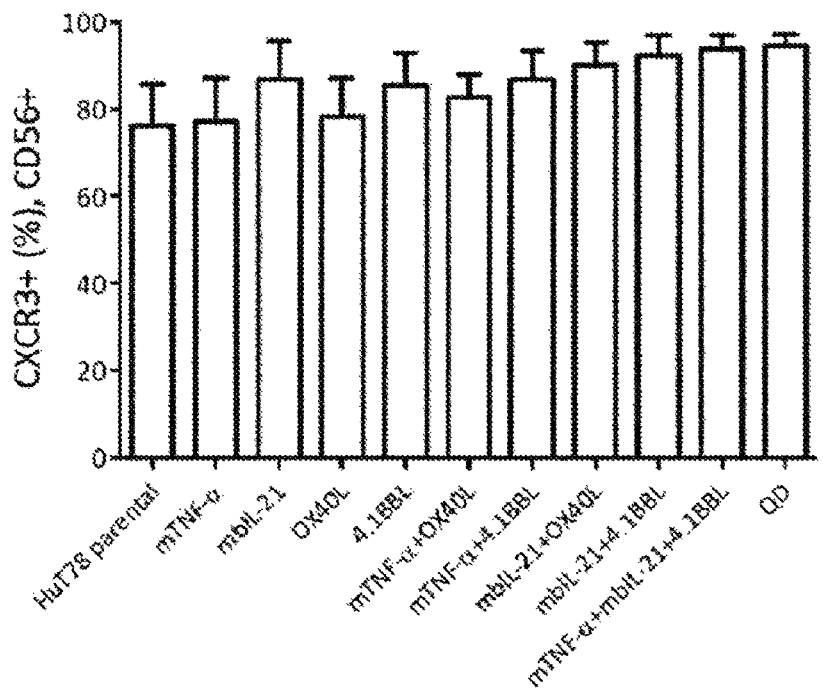

[Fig. 6a]
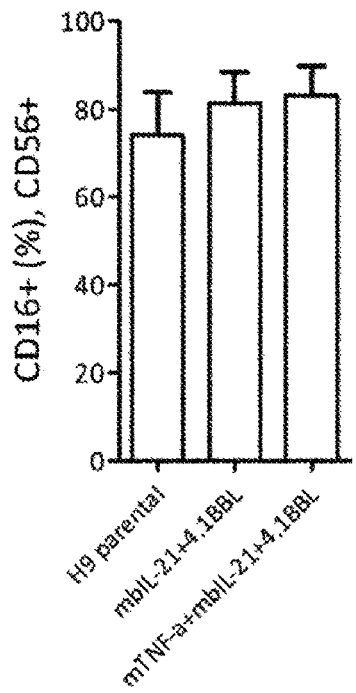
[Fig. 6b]
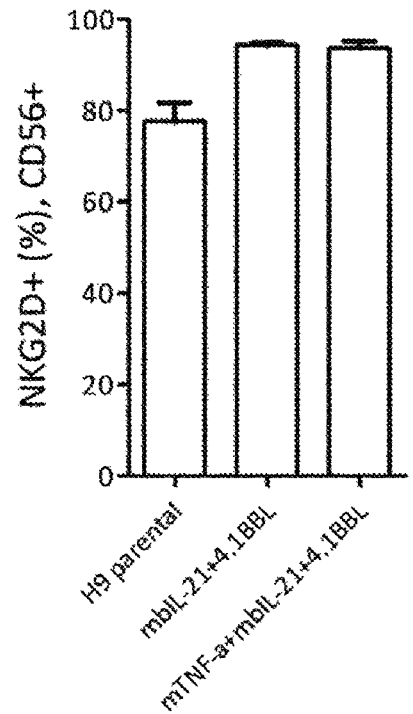

[Fig. 6c]
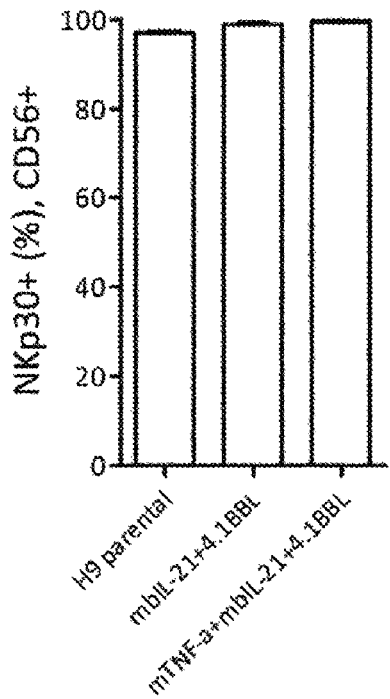
[Fig. 6d]
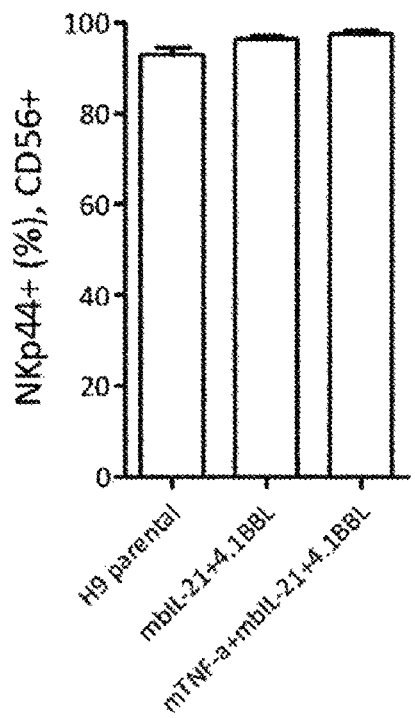

[Fig. 6e]
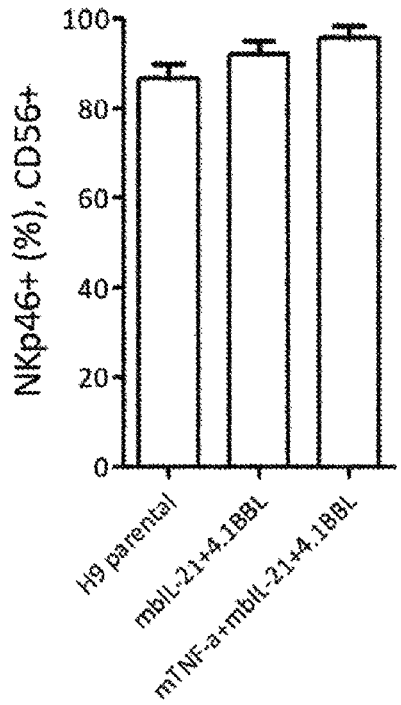
[Fig. 6f]
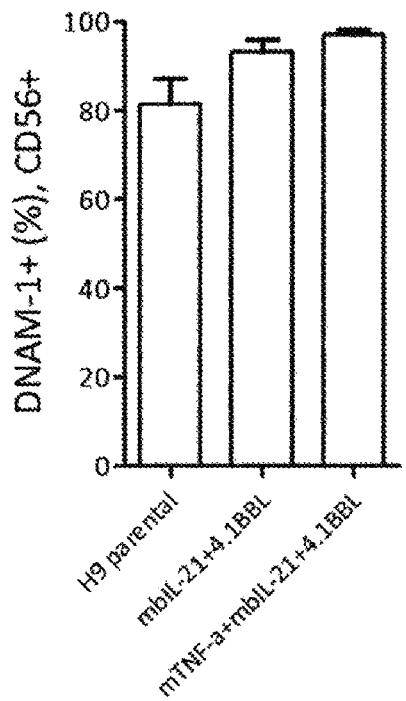

[Fig. 6g]
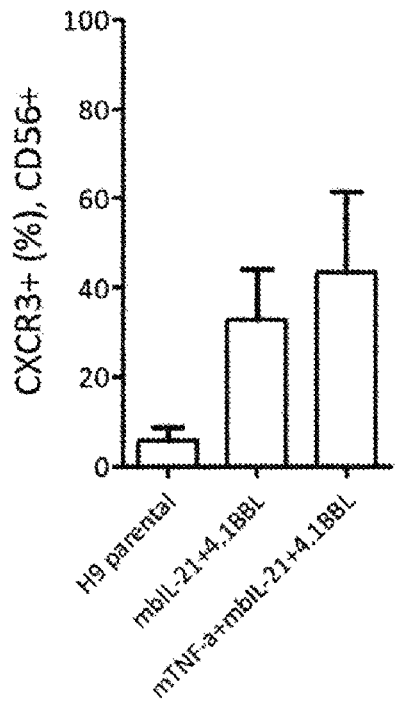
[Fig. 7a]
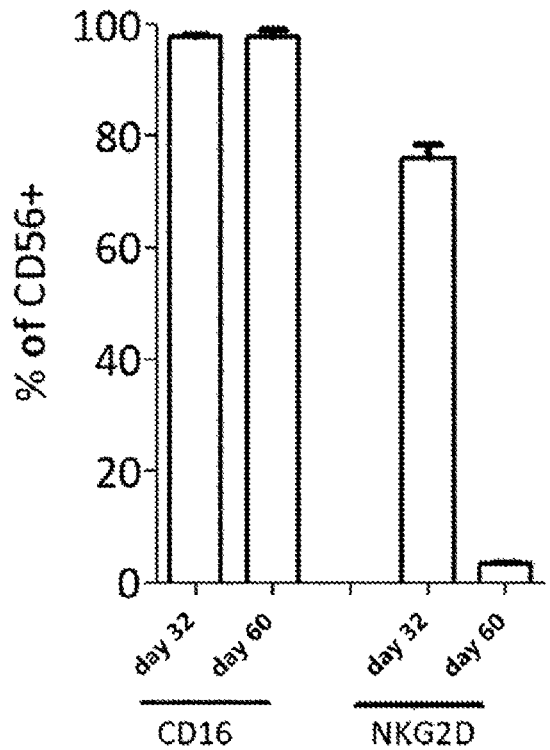

[Fig. 7b]
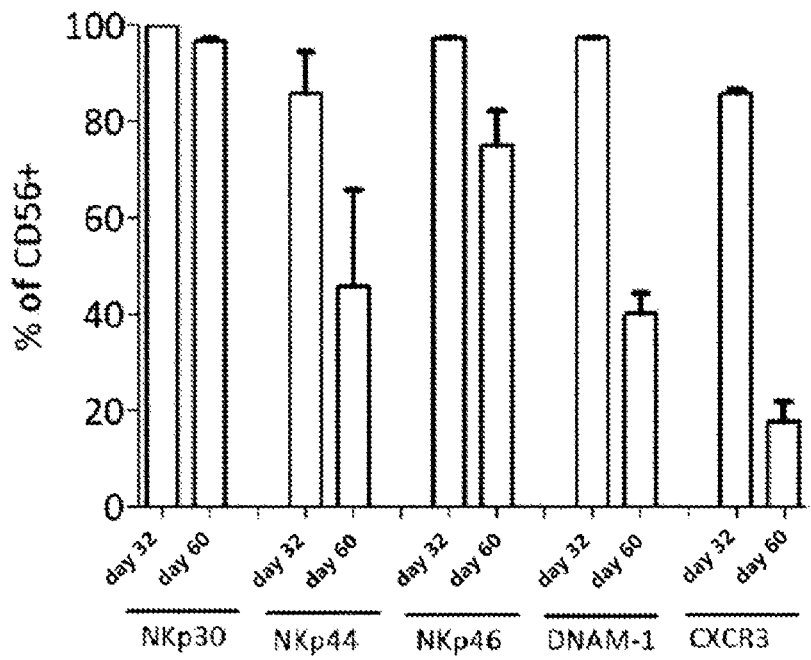
[Fig. 8a]
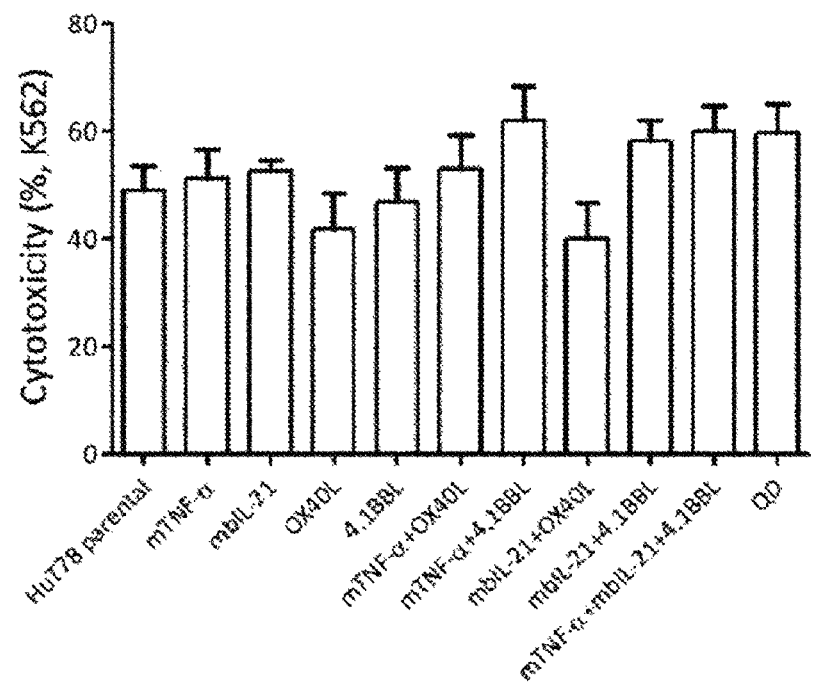

[Fig. 8b]
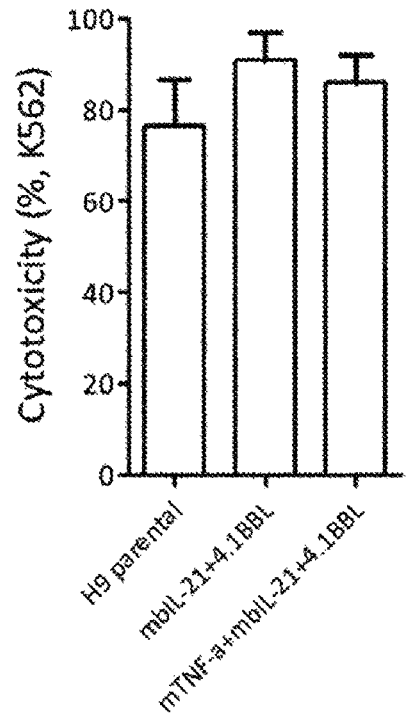
[Fig. 8c]
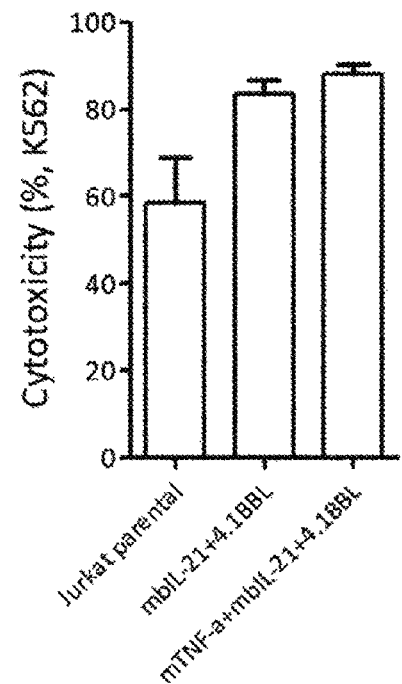

[Fig. 8d]
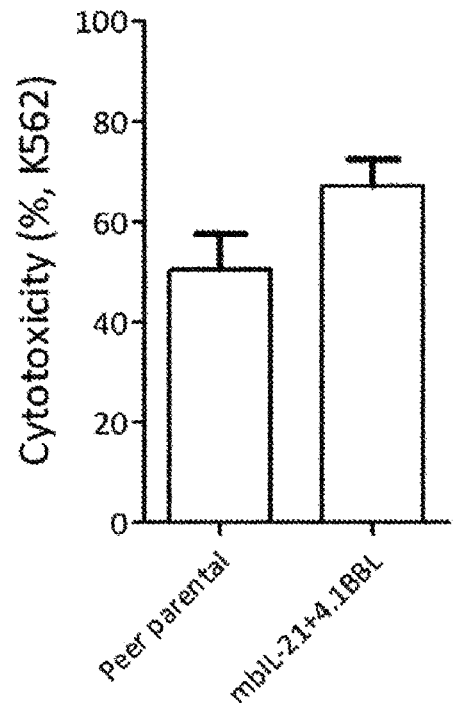
[Fig. 8e]
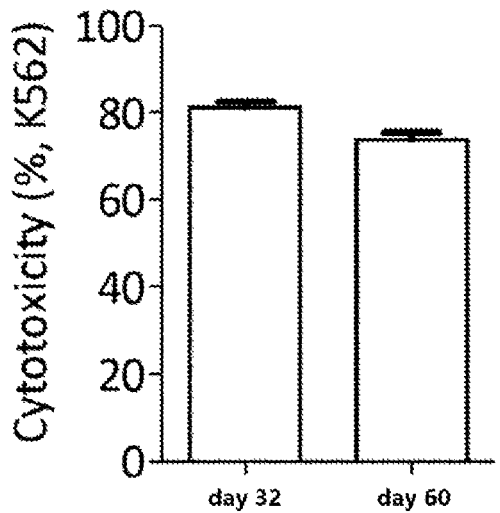

METHOD FOR CULTURING CORD BLOOD-DERIVED NATURAL KILLER CELLS USING TRANSFORMED T-CELLS

TECHNICAL FIELD

The present invention relates to a method for culturing cord blood-derived natural killer cells using transformed T cells.

BACKGROUND ART

Immunotherapies aimed at treating cancer patients and preventing the recurrence of cancer in patients using their own immunity have been developed. Particularly, immunotherapies using natural killer cells that can be mass produced and frozen have also been investigated. Natural killer cells are lymphoid cells that account for about 15% of all peripheral blood lymphocytes and play a key role in the innate immune response.

Specifically, natural killer cells activate dendritic cells and induce cytotoxic T lymphocytes (CTLs) to specifically respond to tumors, eliminating tumor cells. Natural killer cells directly kill malignant tumors such as sarcoma, myeloma, carcinoma, lymphoma, and leukemia. However, the majority of natural killer cells in healthy subjects exist in an inactive state and need to be activated to eliminate tumors. The immune escape mechanism of cancer cells leads to functional defects of natural killer cells in cancer patients.

Thus, the activation of natural killer cells is very important for their use in therapeutic applications. Due to the limited number of natural killer cells in the body, it is essential to develop a technique for large-scale proliferation and freezing of natural killer cells from the blood of healthy subjects or patients.

Ex vivo expansion methods are used to proliferate natural killer cells on a large scale. In addition, research has been conducted on methods for mass culture of natural killer cells using peripheral blood lymphocytes (PBMCs), cord blood (CB) or human-induced pluripotent stem cells as raw materials.

Particularly, cord blood can be obtained from the umbilical cord discarded after childbirth by simple treatment, unlike bone marrow. Due to vitalization of the cord blood storage industry and ease of donor acquisition, methods for culturing natural killer cells from cord blood have been actively investigated.

Specifically, ex vivo expansion of cord blood-derived natural killer cells is based on the proliferation of natural killer cells from mononuclear cells (MNCs) as seed cells or the proliferation of natural killer cells from hematopoietic progenitor cells (CD34+ cells) as seed cells. The approach of using mononuclear cells as seed cells involves the use of interleukin-2 (IL-2), interleukin-15 (IL-15), and FLT-3L alone or in combination to help proliferate natural killer cells. However, this approach has the problems of low proliferation rate and purity (Biossel L. et al., *Biology of Blood and Marrow Transplantation*, 14, 1031-1038, 2008). On the other hand, the approach of using hematopoietic progenitor cells as seed cells is advantageous in terms of proliferation rate and purity but requires along culture period and the use of a mixture of various cytokines and growth factors, making it difficult to commercialize natural killer cells in terms of cost (Fias A M et al., *Experimental Hematology* 36(1):61-68, 2008).

Seed cells such as PBMC, CD3– cells, CD3–CD56+ cells, and CD56+ cells are used for ex vivo expansion culture of natural killer cells. Cytokines such as IL-2, IL-12, IL-15, and IL-21 and OKT-3 antibodies stimulating LPS (Goodier et al., *J. Immunol.* 165(1):139-147, 2000) and CD3 (Condiotti et al., *Experimental Hematol.* 29(1):104-113, 2001) are also used as proliferation factors for natural killer cells. The above-mentioned proliferation factors allow natural killer cells to proliferate about 3-10-fold. However, the proliferation rate alone is insufficient to commercialize natural killer cells for therapeutic applications.

Recent research efforts have focused on methods for mass proliferation of natural killer cells using various types of feeder cells. Peripheral blood mononuclear, EBV-LCL, and K562 cell lines are used as representative feeder cell lines. The K562 cell line is a cell line derived from leukemia lacking HLA. The K562 cell line is a typical target that can be easily attacked by natural killer cells. Most feeder cells used to culture natural killer cells are proliferated by known methods, for example, by expressing 4-1BBL and membrane-bound IL-15 in the K562 cell line (Fujisaki et al., *Cancer Res.* 69(9):4010-4017, 2009), expressing MICA, 4-1BBL, and IL-15 (Gong et al., *Tissue Antigens*, 76(6): 467-475, 2010), and expressing 4-1BBL and membrane-bound IL-21 (Cecele J D et al, *PloSONE*, 7(1):e30264, 2012).

PRIOR ART (Non-patent literature 001) Biossel L. et al., Biology of Blood and Marrow Transplantation, 14, 1031-1038, 2008
(Non-patent literature 002) Fias A. M. et al., Experimental Hematology 36(1):61-68, 2008
(Non-patent literature 003) Goodier et al., J. Immunol., 165(1):139-147, 2000
(Non-patent literature 004) Fujisaki et al., Cancer Res. 69(9):4010-4017, 2009
(Non-patent literature 005) Gong et al., Tissue Antigens, 76(6):467-475, 2010
(Non-patent literature 006) Cecele J D et al, PloSONE, 7(1):e30264, 2012

DETAILED DESCRIPTION OF THE INVENTION

Problems to be Solved by the Invention

Under such circumstances, the inventors of the present invention have succeeded in developing an efficient method for ex vivo proliferation of natural killer cells from cord blood by co-culturing the cord blood-derived natural killer cells with CD4+ T cells expressing a costimulatory factor and a growth factor capable of increasing the proliferation of the natural killer cells.

Specifically, the inventors of the present invention have produced and used transformed CD4(+) T cells as feeder cells to efficiently culture natural killer cells and have found that co-culture of the transformed CD4(+) T cells and cord blood-derived mononuclear cells leads to increases in the proliferation rate and cytotoxicity of natural killer cells. Based on this finding, the present invention has been accomplished.

Means for Solving the Problems

One aspect of the present invention provides a method for culturing natural killer cells including co-culturing transformed CD4+ T cells and seed cells.

A further aspect of the present invention provides natural killer cells produced by the method.

Effects of the Invention

The method of the present invention uses transformed T cells to culture natural killer cells and enables effective proliferation and production of natural killer cells from a small amount of cord blood-derived seed cells. In addition, natural killer cells produced by the method of the present invention have improved cytotoxicity. Therefore, the method of the present invention is useful in commercializing natural killer cells for cell therapy. Furthermore, natural killer cells produced by the method of the present invention are useful for cell therapy.

BRIEF DESCRIPTION OF THE DRAWINGS

FIG. 1a shows the expressions of different genes in the Hut78 cell line, which were determined by FACS.

FIG. 1b shows the expressions of single genes transduced into the Hut78 cell line, which were determined by FACS.

FIG. 1c shows the expressions of double genes mTNF-α/OX40L and mTNF-α/4-1BBL transduced into the Hut78 cell line, which were determined by FACS.

FIG. 1d shows the expressions of double genes mbIL-21/OX40L and mbIL-21/4-1BBL transduced into the Hut78 cell line, which were determined by FACS.

FIG. 1e shows the expressions of triple genes transduced into the Hut78 cell line, which were determined by FACS.

FIG. 1f shows the expressions of quadruple genes transduced into the Hut78 cell line, which were determined by FACS.

FIG. 2a shows the proliferation rates of natural killer cells produced by co-culturing the Hut78 cell line transduced with different genes and cord blood-derived CD3(−) mononuclear cells.

FIG. 2b shows the proliferation rates of natural killer cells produced by co-culturing the H9 cell line transduced with different genes and cord blood-derived CD3(−) mononuclear cells.

FIG. 2c shows the proliferation rates of natural killer cells produced by co-culturing the Jurkat cell line transduced with different genes and cord blood-derived CD3(−) mononuclear cells.

FIG. 2d shows the proliferation rates of natural killer cells produced by co-culturing the Peer cell line transduced with different genes and cord blood-derived CD3(−) mononuclear cells.

FIG. 2e shows the proliferation rates of natural killer cells produced by restimulation at intervals of 14 or 16 days during co-culture of the Hut78 cell line transduced with triple genes and cord blood-derived CD3(−) mononuclear cells.

FIG. 3a shows the viabilities of natural killer cells produced by co-culturing the Hut78 cell line transduced with different genes and cord blood-derived CD3(−) mononuclear cells.

FIG. 3b shows the viabilities of natural killer cells produced by co-culturing the H9 cell line transduced with different genes and cord blood-derived CD3(−) mononuclear cells.

FIG. 3c shows the viabilities of natural killer cells produced by co-culturing the Jurkat cell line transduced with different genes and cord blood-derived CD3(−) mononuclear cells.

FIG. 3d shows the viabilities of natural killer cells produced by co-culturing the Peer cell line transduced with different genes and cord blood-derived CD3(−) mononuclear cells.

FIG. 3e shows the viabilities of natural killer cells produced by restimulations at intervals of 14 or 16 days during co-culture of the Hut78 cell line transduced with triple genes and cord blood-derived CD3(−) mononuclear cells.

FIG. 4a shows the purities (CD3−CD56+) of natural killer cells produced by co-culturing the Hut78 cell line transduced with different genes and cord blood-derived CD3(−) mononuclear cells.

FIG. 4b shows the purities (CD3−CD56+) of natural killer cells produced by co-culturing the H9 cell line transduced with different genes and cord blood-derived CD3(−) mononuclear cells.

FIG. 4c shows the purities (CD3−CD56+) of natural killer cells produced by co-culturing the Jurkat cell line transduced with different genes and cord blood-derived CD3(−) mononuclear cells.

FIG. 4d shows the purities (CD3−CD56+) of natural killer cells produced by co-culturing the Peer cell line transduced with different genes and cord blood-derived CD3(−) mononuclear cells.

FIG. 4e shows the purities (CD3−CD56+) of natural killer cells produced by restimulations at intervals of 14 or 16 days during co-culture of the Hut78 cell line transduced with triple genes and cord blood-derived CD3(−) mononuclear cells.

FIG. 5a shows the activities (CD16+CD56+) of natural killer cells produced by co-culturing the Hut78 cell line transduced with different genes and cord blood-derived CD3(−) mononuclear cells.

FIG. 5b shows the expression levels of NKG2D as a phenotypic marker of natural killer cells produced by co-culturing the Hut78 cell line transduced with different genes and cord blood-derived CD3(−) mononuclear cells.

FIG. 5c shows the expression levels of NKp30 as a phenotypic marker of natural killer cells produced by co-culturing the Hut78 cell line transduced with different genes and cord blood-derived CD3(−) mononuclear cells.

FIG. 5d shows the expression levels of NKp44 as a phenotypic marker of natural killer cells produced by co-culturing the Hut78 cell line transduced with different genes and cord blood-derived CD3(−) mononuclear cells.

FIG. 5e shows the expression levels of NKp46 as a phenotypic marker of natural killer cells produced by co-culturing the Hut78 cell line transduced with different genes and cord blood-derived CD3(−) mononuclear cells.

FIG. 5f shows the expression levels of DNAM-1 as a phenotypic marker of natural killer cells produced by co-culturing the Hut78 cell line transduced with different genes and cord blood-derived CD3(−) mononuclear cells.

FIG. 5g shows the expression levels of CXCR3 as a phenotypic marker of natural killer cells produced by co-culturing the Hut78 cell line transduced with different genes and cord blood-derived CD3(−) mononuclear cells.

FIG. 6a shows the activities (CD16+CD56+) of natural killer cells produced by co-culturing the Hut78 cell line transduced with different genes and cord blood-derived CD3(−) mononuclear cells.

FIG. 6b shows the expression levels of NKG2D as a phenotypic marker of natural killer cells produced by co-culturing the H9 cell line transduced with different genes and cord blood-derived CD3(−) mononuclear cells.

FIG. 6c shows the expression levels of NKp30 as a phenotypic marker of natural killer cells produced by co-culturing the H9 cell line transduced with different genes and cord blood-derived CD3(−) mononuclear cells.

FIG. 6d shows the expression levels of NKp44 as a phenotypic marker of natural killer cells produced by co-culturing the H9 cell line transduced with different genes and cord blood-derived CD3(−) mononuclear cells.

FIG. 6e shows the expression levels of NKp46 as a phenotypic marker of natural killer cells produced by co-culturing the H9 cell line transduced with different genes and cord blood-derived CD3(−) mononuclear cells.

FIG. 6f shows the expression levels of DNAM-1 as a phenotypic marker of natural killer cells produced by co-culturing the H9 cell line transduced with different genes and cord blood-derived CD3(−) mononuclear cells.

FIG. 6g shows the expression levels of CXCR3 as a phenotypic marker of natural killer cells produced by co-culturing the H9 cell line transduced with different genes and cord blood-derived CD3(−) mononuclear cells.

FIG. 7a shows the activities (CD16+CD56+) of natural killer cells produced by restimulations at intervals of 14 or 16 days during co-culture of the Hut78 cell line transduced with triple genes and cord blood-derived CD3(−) mononuclear cells and the expression levels of NKG2D as a phenotypic marker of the natural killer cells.

FIG. 7b shows the expression levels of NKp30, NKp44, NKp46, DNAM-1, and CXCR3 as phenotypic markers of natural killer cells produced by restimulations at intervals of 14 or 16 days during co-culture of the Hut78 cell line transduced with triple genes and cord blood-derived CD3(−) mononuclear cells.

FIG. 8a shows the cytotoxicities of natural killer cells, which were produced by co-culturing the Hut78 cell line transduced with different genes and cord blood-derived CD3(−) mononuclear cells, to tumor cells.

FIG. 8b shows the cytotoxicities of natural killer cells, which were produced by co-culturing the H9 cell line transduced with different genes and cord blood-derived CD3(−) mononuclear cells, to tumor cells.

FIG. 8c shows the cytotoxicities of natural killer cells, which were produced by co-culturing the Jurkat cell line transduced with different genes and cord blood-derived CD3(−) mononuclear cells, to tumor cells.

FIG. 8d shows the cytotoxicities of natural killer cells, which were produced by co-culturing the Peer cell line transduced with different genes and cord blood-derived CD3(−) mononuclear cells, to tumor cells.

FIG. 8e shows the cytotoxicities of natural killer cells, which were produced by restimulations at intervals of 14 or 16 days during co-culture of the Hut78 cell line transduced with triple genes and cord blood-derived CD3(−) mononuclear cells, to tumor cells.

BEST MODE FOR CARRYING OUT THE INVENTION

The present invention will now be described in detail.

One aspect of the present invention provides a method for culturing natural killer cells including co-culturing transformed CD4+ T cells and seed cells.

The transformed CD4+ T cells may express at least one gene selected from the group consisting of the 4-1BBL, mbIL-21, OX40L, and mTNF-α genes.

Specifically, a single gene may be expressed in the transformed CD4+ T cells. In this case, the gene may be 4-1BBL, mbIL-21, OX40L or mTNF-α. Alternatively, two genes may be expressed in the transformed CD4+ T cells. In this case, the gene combination may be mbIL-21/4-1BBL, 4-1BBL/OX40L, mTNF-α/4-1BBL, mbIL-21/OX40L, mbIL-21/mTNF-α or mTNF-α/OX40L. In the Examples section that follows, mbIL-21/4-1BBL, mTNF-α/OX40L, mTNF-α/4-1BBL, and mbIL-21/OX40L as gene combinations were transduced into T cells.

Alternatively, three genes may be expressed in the transformed CD4+ T cells. In this case, the gene combination may be 4-1BBL/mbIL-21/OX40L, mbIL-21/OX40L/mTNF-α, mTNF-α/mbIL-21/4-1BBL or 4-1BBL/OX40L/mTNF-α. In the Examples section that follows, mTNF-α/mbIL-21/4-1BBL was transduced into T cells.

Alternatively, four genes may be expressed in the transformed CD4+ T cells. In this case, the gene combination may be mTNF-α/mbIL-21/OX40L/4-1BBL. In the Examples section that follows, mTNF-α/mbIL-21/OX40L/4-1BBL was transduced into T cells.

The term "4-1BBL" as used herein refers to a ligand that forms a trimer and binds to 4-1BB as a receptor. 4-1BBL is a member belonging to the TNF superfamily (TNFSF) and is also called CD137L. The 4-1BBL gene may be derived from human.

Specifically, the 4-1BBL gene may be NCBI Reference Sequence: NM_003811 but is not limited thereto. The 4-1BBL gene may have a nucleotide sequence encoding the amino acid sequence set forth in SEQ ID NO: 1. The encoding nucleotide sequence may be set forth in SEQ ID NO: 2.

The term "mbIL-21" as used herein refers to IL-21 designed to bind to the cell membrane. mbIL-21 may be a fusion protein in which IL-21 and a transmembrane protein are fused together. The transmembrane protein may be CD8α, specifically a transmembrane domain of CD8α.

Specifically, the IL-21 gene may be NCBI Reference Sequence: NM_021803.3 but is not limited thereto. The CD8α gene may be NCBI Reference Sequence: NM_001768 but is not limited thereto. The mbIL-21 is expressed in the form of IL-21 that binds to the cell membrane. The mbIL-21 gene may have a nucleotide sequence encoding the amino acid sequence set forth in SEQ ID NO: 3. The encoding nucleotide sequence may be set forth in SEQ ID NO: 4.

The term "OX40L" as used herein refers to a ligand that binds to OX40. OX40L is also called TNFSF4, gp34, TXGP1, CD252 or CD134L. Specifically, the OX40L gene may be NCBI Reference Sequence: NM_003326 but is not limited thereto. The OX40L gene may have a nucleotide sequence encoding the amino acid sequence set forth in SEQ ID NO: 5. The encoding nucleotide sequence may be set forth in SEQ ID NO: 6.

The term "mTNF-α" as used herein refers to a gene in which alanine-valine, a tumor necrosis factor-alpha-converting enzyme (TACE) recognition site in the amino acid sequence of tumor necrosis factor-alpha, is point mutated to proline-valine on DNA. The alanine mutated to proline is randomly selected.

Specifically, the mTNF-α gene may have a nucleotide sequence encoding the amino acid sequence set forth in SEQ ID NO: 8. The encoding nucleotide sequence may be set forth in represented by SEQ ID NO: 9.

The 4-1BBL, mbIL-21, OX40L or mTNF-α gene may be transduced through a recombinant lentivirus. The gene transduction vector is not limited to a recombinant lentivirus.

The gene(s) may be transfected into the cells by biochemical, physical or virus-mediated transfection. FuGene6 (Roche, USA), Lipofectamine™ 2000 (Invitrogen, USA) or ExGen 500 (MBI Fermentas International Inc. CANADA)

may be used for biochemical transfection. Lipid-mediated transfection using lipofectamine may also be used.

The term "vector" as used herein refers to a gene construct containing an essential regulatory element operably linked such that that a gene insert introduced into the vector is expressed. The vector may be an expression vector that can express a target gene in a cell into which the vector has been introduced.

The gene-containing expression vector may be any expression vector that can express the gene in the CD4+ cell line. In the Examples section that follows, a pCDH-CMV-MCS-EF1-Puro (SBI, CD510B-1) or pCDH-CMV-MCS-EF1-Neo (SBI, CD514B-1) lentiviral vector was used as the expression vector.

The lentivirus refers to a virus belonging to the family of retroviruses characterized by a long incubation period. The lentivirus can deliver genetic information to the DNA of the host cell. The use of the lentivirus is one of the most effective approaches to use gene delivery vectors that can replicate in non-dividing cells.

The CD4+ T cells may be ex vivo isolated CD4+ T cells, ex vivo expanded cultured CD4+ T cells or CD4+ cell line (T lymphoma cell line). The CD4+ T cells may be auxiliary T cells and may be hybridomas obtained by fusion with cancer cells. Specifically, the CD4+ T cells may be selected from the group consisting of Hut78, H9, Jurkat, Loucy, Molt-3, Molt-13, Peer, RPMI8402, and TALL-01 cells. Preferably, the CD4+ T cells are Hut78, H9, Jurkat or Peer cells.

The term "feeder cell" as used herein refers to a cell that does not proliferate but can produce various metabolites to help the proliferation of a target cell due to its metabolic activity. The feeder cells are also called culture auxiliary cells and may be transformed CD4+ T cells that express at least one gene selected from the group consisting of the 4-1BBL, mbIL-21, OX40L, and mTNF-α genes.

The T cells as feeder cells may be inactivated cells that are inhibited from division/proliferation or may be non-inactivated cells. Preferably, the T cells are inactivated to ensure safety. The inactivation may be accomplished by any suitable method known in the art, for example, by irradiation with gamma-rays. Most of the non-inactivated T cells are tumor cells that can be killed by activated natural killer cells during culture.

The term "seed cell" as used herein refers to a cell that can proliferate to natural killer cells through appropriate culture. Specifically, the seed cells may be cord blood-derived mononuclear cells or cord blood-derived natural killer cells but are not limited thereto. The seed cells are preferably CD3(−) cells from which CD3(+) cells are eliminated.

According to the method of the present invention, natural killer cells may be cultured by mixing the feeder cells with the seed cells in a ratio ≥0.1:1. The ratio of the feeder cells to the seed cells may be specifically 0.1:1 to 50:1, more specifically 0.5:1 to 40:1, even more specifically 1:1 to 30:1, most specifically 2:1 to 20:1. In one embodiment, the ratio of the feeder cells to the seed cells may be 2.5:1 but is not particularly limited thereto. The "ratio" is based on the numbers of the feeder cells and the seed cells.

According to the method of the present invention, natural killer cells may be cultured by mixing the seed cells with the feeder cells only once for 5 to 60 days or by mixing the seed cells with the feeder cells twice or more for at least 60 days. Preferably, the culture is performed by mixing the seed cells with the feeder cells only once for 14 to 21 days but is not limited to these conditions.

According to the method of the present invention, natural killer cells may be cultured with a T lymphoma cell line in a general animal cell culture medium such as AIM-V medium, RPMI1640 medium, CellGro SCGM, X-VIVO20 medium, IMDM or DMEM. Suitable substances may be added to the culture medium. The suitable substances may be an antibody that has low affinity for and stimulates T cells and an interleukin but are not limited thereto.

The term "antibody that has low affinity for and stimulates T cells" as used herein refers to a protein that specifically responds to CD3 antigens belonging to a group of molecules that associate with T cell receptors (TCRs) to form antigen recognition complexes. The CD3 molecules have longer intracellular regions than the TCRs and play a role in transmitting antigen recognition signals to cells.

The antibody that has low affinity for and stimulates T cells is preferably an anti-CD3 antibody. Specifically, the anti-CD3 antibody may be OKT-3, UCHT1 or HIT3a.

The term "interleukin (IL)" as used herein refers to a biologically active proteinaceous substance produced by immunocompetent cells such as lymphocytes, monocytes, and macrophages. The interleukin belongs to a group of cytokines and may be IL-2, IL-15, IL-12, IL-18 or IL-21.

In the Examples section that follows, OKT-3 and IL-2 were added for culture. The antibody may be added at a concentration of 0.1 ng/ml to 1,000 ng/ml, preferably 10 ng/μl. The interleukin may be added at a concentration of 10 U/ml to 2,000 U/ml, preferably 1,000 U/ml. The medium may be supplemented with serum or plasma and an additional growth factor that supports the proliferation of lymphocytes. The serum or plasma is not particularly limited to a particular type and is selected from commercially available animal-derived serum and plasma products. The serum or plasma is preferably human-derived serum or plasma.

The term "culture" as used herein refers to cell growth under appropriately artificially controlled environmental conditions. The transformed CD4+ T cells may be cultured by a suitable method widely known in the art. Specifically, the culture may be performed in a batch or fed batch process or may be continuously performed in a repeated fed batch process.

Progenitor cells suitable for the culture medium may be used. The above-described raw materials may be added to the culture in a batch, fed-batch or continuous manner during culture by an appropriate method, but the manner of addition is not particularly limited. A basic compound such as sodium hydroxide, potassium hydroxide or ammonia or an acidic compound such as phosphoric acid or sulfuric acid may be used in an appropriate manner to adjust the pH of the culture.

The use of the T cells as feeder cells selectively induces the culture of natural killer cells from the seed cells. When compared to the use of PBMC feeder cells from a donor, the use of the T cells as feeder cells enables more stable culture of natural killer cells without any difference depending on who is the donor during proliferation. Further, the use of MNCs from a donor as feeder cells makes ex vivo culture of cord blood seed cells difficult. Therefore, the use of T cells as feeder cells in the method of the present invention can ensure a large amount of therapeutic natural killer cells in an efficient and stable manner.

A further aspect of the present invention provides natural killer cells produced by the method.

The natural killer cells can be frozen and do not lose their functions even when thawed. In addition, the natural killer cells have increased cytotoxicity against tumor cell lines and secrete a large amount of cytokines due to their ability to express a high level of activating receptors such as NKp46, and as a result, their outstanding anticancer activity can be expected. Therefore, when activated, the clinically applicable natural killer cells can be used in a large amount to produce effective cell therapeutic agents for tumors.

The natural killer cells can be used as active ingredients of a pharmaceutical composition for preventing or treating an infectious disease. In this case, the natural killer cells are present in an amount of 10 to 95% by weight, based on the total weight of the composition. The composition may further include one or more active ingredients with the same or similar functions.

The pharmaceutical composition may be formulated with one or more pharmaceutically acceptable carriers for administration.

The dose of the pharmaceutical composition can be adjusted depending on various factors, including type and severity of the disease, kinds and amounts of the active ingredients and other ingredients, type of the formulation, patient's age, weight, general health, sex, and diet, time and route of administration, secretion rate of the composition, treatment period, and presence of a concomitant drug. For the desired effect, the natural killer cells are used in an amount of $0.01 \times 10^7$ cells/kg to $1.0 \times 10^9$ cells/kg or $0.5 \times 10^7$ cells/kg to $1.0 \times 10^8$ cells/kg. The composition can be administered in single or divided doses per day.

The pharmaceutical composition may be administered to subjects by various methods known in the art. The route of administration may be appropriately selected by those skilled in the art in consideration of the mode of administration, the volume of the body fluid, the viscosity of the composition, and other factors.

The present invention will be explained in detail with reference to the following examples. However, these examples are provided for illustrative purposes only and are not intended to limit the scope of the present invention.

Example 1. Production of Recombinant Lentiviruses

Example 1.1. Construction of Recombinant Lentiviral Vectors pCDH-CMV-MCS-EF1-Puro (SBI, CD510B-1) or pCDH-CMV-MCS-EF1-Neo (SBI, CD514B-1) was used as a lentiviral vector. 4-1BBL (TNF superfamily member 9, TNFSF9), mbIL-21 (membrane bound IL-21), OX40L (TNF superfamily member 4 (TNFSF4) transcript variant 1), and mTNF-α (membrane bound TNF alpha) were used as genes for transduction.

Specifically, a 4-1BBL gene expression vector (Origene, RC211160) was used for the 4-1BBL gene (SEQ ID NO: 2) and a pcDNA3.1 vector (Genscript, US) carrying a codon-optimized mbIL-21 gene sequence was used for the mbIL-21 gene (SEQ ID NO: 4). Synthesis of the OX40L gene (SEQ ID NO: 6) was requested to Bioneer.

For the mTNF-α gene (SEQ ID NO: 9), RNA was extracted from peripheral blood mononuclear cells (PBMCs) and then CDS was obtained by reverse transcriptase (RT)-PCR. TNF-α was cleaved with tumor necrosis factor-alpha-converting enzyme (TACE) for secretion. For this cleavage, alanine-valine, a TACE recognition site in the amino acid sequence of TNF-α, was point mutated to proline-valine on DNA, such that TNF-α remained attached to the cell membrane. The point mutation was performed by substituting the guanine and adenine residues at positions 226 and 228 in the human mTNF-α gene (SEQ ID NO: 7) with cytosine and guanine, respectively.

The coding sequence (CDS) of each gene was amplified by PCR using primers suitable for the gene (Table 1).

TABLE 1

| Gene | Primers | Sequence (5'→3') | SEQ ID NO: |
|------|---------|------------------|------------|
| 4-1BBL | 4-1BBL Forward | TCTAGAGCTAGCGAATTCGCCACCATG GAATACGCCTCTGACGCTT | 10 |
|  | 4-1BBL Reverse | TTCGCGGCCGCGGATCCTTATTCCGAC CTCGGTGAAGG | 11 |
| mbIL-21 | mbIL-21 Forward | TAGAGCTAGCGAATTCGCCACCGCCAC CATGGCTCTGCCC | 12 |
|  | mbIL-21 Reverse | TCGCGGCCGCGGATCCTCAATACAGGG TGATGACC | 13 |
| OX40L | OX40L Forward | TAGAGCTAGCGAATTCGCCACCATGGA ACGGGTGCAAC | 14 |
|  | OX40L Reverse | TCGCGGCCGCGGATCCTCACAAGACAC AGAACTCCCC | 15 |
| mTNF-α | mTNF-α Forward | TAGAGCTAGCGAATTCGCCACCGCCAC CATGGCTCTGCCC | 16 |
|  | mTNF-α Reverse | TCGCGGCCGCGGATCCTCACAGGGCAA TGATCCC | 17 |

The gene and the lentiviral vector were treated with EcoRI and BamHI as restriction enzymes, followed by ligation with an In-Fusion HD cloning kit (Clontech, 639649). The ligated lentiviral vector was transformed into DH5α competent cells, followed by culture. Plasmid DNA was isolated from the transformed DH5α competent cells using a plasmid mini-prep kit (MACHEREY-NAGEL/ 740422.50). All plasmid DNA samples were outsourced for sequencing to confirm matching of the DNA sequences. The desired genes were transduced into cLV-CMV-MCS-IRES-Puro (puromycin), cLV-CMV-MCS-IRES-Neo (neomycin), and cLV-CMV-MCS-IRES-Bsd (blasticidin) in the same manner as described above. This gene transduction was outsourced to an external manufacturer.

Example 1.2. Production of Concentrated Lentiviruses

In this example, recombinant lentiviruses were produced. First, the $1.5 \times 10^6$-$2 \times 10^6$ cells of the 293T cell line were inoculated into a 75T flask (Nunc, 156499) 2 days before transfection. The cells were cultured in an incubator at 5% $CO_2$ and 37° C. When the 293T cells were cultured to a confluency of ~80-90%, the medium was replaced with 6 ml of OPTI-MEM (Gibco, 31985-088). Cells were cultured at 37° C. and 5% $CO_2$ for 30 min. A DNA mixture and a lipofectamine mixture (lipofectamine 2000, Life technologies, 11668500) were prepared as shown in Table 2.

TABLE 2

| Mixture | Components |
|---------|------------|
| DNA mixture | 6 μg target DNA, 6 μg Gag, 6 μg REV, 3 μg VSVG, 1 ml OPTI-MEM |
| Lipofectamine mixture | 36 μl lipofectamine 2000, 1 ml OPTI-MEM |

The components of each mixture were sufficiently mixed in a vortexer and left standing at room temperature for 3 min. Thereafter, the two mixtures were mixed together and allowed to stand at room temperature for at least 20 min. The 293T cells cultured in 6 ml of OPTI-MEM medium were treated with 2 ml of the DNA/lipofectamine mixture. After 4 h, the medium was replaced with DMEM (Gibco, 11995073) supplemented with 10% (v/v) FBS. Cells were cultured at 37° C. and 5% $CO_2$ for 48 h. 8 ml of the culture solution of 293T cells was collected and passed through a 0.45 μm filter (Millipore, SLHP033RS). The filtrate was concentrated to ≤250 μl with an Amicon Ultra-15 Centrifugal Filter Unit with Ultracel-100 membrane (Merckmillipore, UFC910096). The concentrated virus was aliquoted in appropriate amounts and stored at −80° C.

Example 2. Production of Transgenic T Cells

Example 2.1. Lentiviral Infection $0.5 \times 10^6$ cells of the cultured cell line, 1 ml of OPTI-MEM, 50 μl of the thawed lentiviral solution, and 10 μg/ml polybrene (Santa Cruz, C2013) were mixed and plated in a 6-well plate (Nunc, 140675), followed by spinoculation at 1800×g and 32° C. for 90 min. Then, cells were cultured in an incubator at 5% $CO_2$ and 37° C. for 2 h. The medium was replaced with a new one, followed by culture for 48 h.

Hut78 cell line (ATCC, TIB-161™) was cultured in IMDM (ATCC, 30-2005) supplemented with 20% (v/v) FBS. During subculture, the cell density was maintained at $1.5 \times 10^5$-$2.0 \times 10^5$ cells/ml. H9 cell line (ATCC, HTB-176™) and Jurkat cell line (ATCC, TIB-152™) were cultured in RPMI1640 (ATCC, 30-2001) medium supplemented with 10% (v/v) FBS and their cell densities were maintained at $1.0 \times 10^5$-$1.5 \times 10^5$ cells/ml and $0.5 \times 10^5$-$1.0 \times 10^5$ cells/ml during subculture, respectively. Peer cell line was cultured in RPMI1640 medium supplemented with 20% (v/v) FBS. During subculture, the cell density was maintained at $3.0 \times 10^5$-$5.0 \times 10^5$ cells/ml. All cell lines were subcultured at intervals of 2-3 days. 75T flasks were used as culture vessels and the volumes of the media were maintained at 15-20 ml.

The cell lines infected with recombinant lentiviruses were screened with antibiotics (Table 3).

The antibiotics used for the transgenic cell lines are shown in Table 3.

Example 2.2. Confirmation of Expressions of the Transduced Genes

In this example, the expressions of the transduced genes were confirmed by flow cytometry. Each of the cell lines subcultured in Example 2.1 was collected and centrifuged at 1,200 rpm for 5 min. Then, the culture solution was removed by suction. 2% (v/v) FBS was added to PBS to prepare a FACS buffer. Cells were counted after dilution with 1 ml of the FACS buffer. Cells were diluted to a density of $5 \times 10^6$ cells/ml with the FACS buffer. The diluted cell solution was added to 5 ml FACS tubes (Falcon, 352052) (100 μl per tube). Cells were stained with anti-human TNF-α (membrane)-PE (R&D systems, FAB210P), anti-human OX40L-PE (BD, 558184), anti-human 4-1BBL-PE (BD, 559446), anti-human IL-21-PE (eBioscience, 12-7219-42), 7-AAD (Beckman coulter, IM3630c), PE mouse IgG1 κ isotype control (BD Pharmingen, 555749), and PerCP-Cy5.5 mouse IgG1 κ isotype control (BD, 550795) antibodies. The expression level of the gene was analyzed by FACS (FIGS. 1a to 1f).

The expressions of the transduced genes were confirmed by real time (RT)-qPCR. To this end, each of the cell lines subcultured in Example 2.1 was collected and centrifuged at 1,200 rpm for 5 min. Then, the culture solution was removed by suction. Cells were counted after dilution with PBS. RNA was extracted from $1 \times 10^6$ cells using an RNA prep kit and quantified. cDNA was synthesized using a cDNA synthesis kit. RT-qPCR was performed using the synthesized cDNA. Primers used for the RT-qPCR are shown in Table 4.

TABLE 4

| | Primers | Sequence (5'→3') | SEQ ID NO: |
|---|---|---|---|
| 4.1BBL | Forward primer | TCTGAGACAGGGCATGTTTG | 18 |
| | Reverse primer | CCACCAGTTCTTTGGTGTCC | 19 |
| mTNF-α | Forward primer | AACCTCCTCTCTGCCATCAA | 20 |
| | Reverse primer | ATAGTCGGGCCGATTGATCT | 21 |

TABLE 3

| | Combination of transduced genes | Vector used | Cell line | Concentration of antibiotic used |
|---|---|---|---|---|
| Single gene expression | mTNF-α-mbIL-21 | pCDH (System Biosciences, SBI) | Hut78 | 0.5 μg/ml puromycin (Life technologies, A1113802) |
| | OX40L4-1BBL | pCDH (System Biosciences, SBI) | Hut78 | 1 mg/ml G148 (Sigma Aldrich, A1720-5G) |
| Double gene expression | mTNF-a/OX40L | pCDH (System Biosciences, SBI) | Hut78 | 0.5 μg/ml puromycin |
| | mbIL-21/OX40L | | | 1 mg/ml G418 |
| | mTNF-a/4-1BBL | | | |
| | mbIL-21/4-1BBL | cLV (Sirion) | Hut78 H9 Jurkat Peer | 6 μg/ml Blasticidin (Invitrogen, R210-01) 1 mg/ml G148 |
| Triple gene expression | mTNF-a/mbIL-21/ 4-1BBL | cLV (Sirion) | Hut78 H9 Jurkat | 0.5 μg/ml puromycin 6 μg/ml Blasticidin 1 mg/ml G418 |
| Quadruple gene expression | mTNF-a/mbIL-21/ OX40L/4-1BBL | mTNF-a/mbIL-21/ 4-1BBL: cLV Ox40L: pCDH | Hut78 | 0.5 μg/ml puromycin 6 μg/ml Blasticidin 1 mg/ml G418 |

TABLE 4-continued

| Primers | | Sequence (5'→3') | SEQ ID NO: |
|---|---|---|---|
| mbIL-21 | Forward primer | TGGAAACAATGAGCGAATCA | 22 |
| | Reverse primer | AACCGCTCCAGGAACTCTTT | 23 |
| hTOP1 | Forward primer | CCAGACGGAAGCTCGGAAAC | 24 |
| | Reverse primer | GTCCAGGAGGCTCTATCTTGAA | 25 |

The expression levels of the transduced genes in the cell lines are shown in Table 5.

TABLE 5

| Ct value | TOP1 | mTNF-α | mbIL-21 | 4.1BBL |
|---|---|---|---|---|
| H9 | 20.3 | 21.5 | n.d | n.d |
| H9-mbIL-21-4.1BBL | 20.0 | 22.2 | 19.5 | 19.4 |
| H9-mTNF-α-mbIL-21-4.1BBL | 19.9 | 18.2 | 18.1 | 18.2 |
| Jurkat | 20.1 | 30.7 | n.d | n.d |
| Jurkat-mbIL-21-4.1BBL | 27.4 | 37.0 | 36.4 | 34.1 |
| Jurkal-mTNF-α-mbIL-21-4.1BBL | 20.4 | 19.8 | 19.2 | 19.8 |
| Peer | 21.4 | 26.2 | 34.2 | 34.9 |
| Peer-mbIL-21-4.1BBL | 26.8 | 33.8 | 29.0 | 25.6 |

* n.d: not detected

As can be seen from the results in Table 5, high expression levels of the genes were induced when transduced into the cell lines.

Example 3. Co-Culture of CD3(−) PBMCs and Transgenic T Cells

Example 3.1. Preparation of Cord Blood-Derived CD3(−) PBMCs as Seed Cells

Cord blood donated for research purposes was placed in a 50 ml tube and centrifuged at 1,500 rpm for 10 min. After removal of the supernatant plasma, phosphate buffered saline (PBS, LONZA, 17-516Q) was added in a 1:1 ratio. Thereafter, cord blood mononuclear cells (MNCs) were isolated by ficoll density gradient centrifugation (Ficoll-Paque Plus, GE Healthcare, 17-1440-03) and the cell number was measured using an ADAM cell counter system (Nano Entec).

Seed cells from which CD3(+) cells were eliminated were obtained by the following procedure. First, $5 \times 10^7$ cord blood mononuclear cells were transferred to a new 50 ml tube and centrifuged at 1,200 rpm and 4° C. for 5 min. 2% (v/v) FBS and 2 mM EDTA were mixed in PBS to prepare a MACS running buffer. After completion of the centrifugation, 400 μl of the MACS running buffer and 100 μl of CD3 magnetic beads (Miltenyi biotech, 130-050-101) were added to the pellets and incubation was allowed to proceed at 4° C. for 20 min. The culture was washed with 10 ml of the MACS running buffer, centrifuged at 13,500 rpm and 4° C. for 8 min, and suspended in 0.5 ml of the MACS running buffer.

Cells were isolated on VarioMACS (Miltenyi Biotech) equipped with a CS column (column, Miltenyi Biotech, 130-041-305). Cells were recovered by washing the column until the final volume reached 20 ml. The recovered cells were placed in a new 50 ml tube, centrifuged at 1,200 rpm and 4° C. for 5 min, and suspended in a freezing medium. The cells were counted using an ADAM cell counter system. $5 \times 10^6$ cells per vial were frozen in liquid nitrogen.

The frozen CD3(−) cord blood mononuclear cells in each vial were thawed in a thermostatic bath at 37° C., transferred to a 50 ml tube, suspended in PBS containing 0.6% (v/v) citrate-dextrose solution (ACD, Sigma-Aldrich, C3821), 0.2% (v/v) fetal serum bovine (FBS), and 2 mM EDTA, and centrifuged at 1,500 rpm and 4° C. for 10 min. The CD3(−) cord blood mononuclear cells were suspended in CellGro medium (Cellgenix, 20802-0500) and the cell number was measured using an ADAM cell counter system. The CD3(−) cord blood mononuclear cells were suspended to a density of $1 \times 10^6$ cells/ml in CellGro medium.

Example 3.2. Co-Culture of the CD3(−) Cord Blood Mononuclear Cells and the Transgenic T Cells The transgenic T cells produced in Example 2 were recovered from the culture flask and centrifuged at 1,200 rpm and 4° C. for 5 min. Thereafter, the cells were suspended in CellGro medium and counted using an ADAM cell counter system. The transgenic T cells were suspended to a density of $2.5 \times 10^6$ cells/ml in CellGro medium and were then inactivated by irradiation with gamma-rays at 20,000 cGy.

Natural killer cells were cultured by the following procedure. First, 1,000 IU of IL-2 (Proleukin Injection, Novartis Korea) and 10 ng/ml OKT-3 (eBioscience, 16-0037-85) were plated in a plastic culture plate. On day 0 of culture, the CD3(−) cord blood mononuclear cells and the transgenic T cells (each 0.25 ml) were added in a ratio of 1:2.5 and 0.25 ml of CellGro medium supplemented with 2% (v/v) human plasma was added. Cells were cultured statically in an incubator at 37° C. for 4 days.

On day 4 of culture, the equal amount of CellGro medium supplemented with 1% (v/v) human plasma and 1,000 IU/ml IL-2 was added, followed by stationary culture. Thereafter, cells were counted at intervals of 2-3 days. CellGro medium supplemented with 1% (v/v) human plasma and 1,000 IU/ml IL-2 was added and suspension culture was performed until day 21 such that the cell density was $1 \times 10^6$ cells/ml. When cells of the Jurkat cell line or Peer cell line were used as feeder cells, suspension culture was continued until day 11. When cells of the transgenic H9 and Hut78 cell lines were as feeder cells, suspension culture was continued until day 21.

The proliferation rates of the cultured natural killer cells were compared based on the total nucleated cells (TNCs). As a result, the proliferation rate of natural killer cells increased as much as 93-fold when co-cultured with the non-transgenic Hut78 cell line. In contrast, the proliferation rate of natural killer cells increased significantly when co-cultured with the Hut78 cell line transduced with one or more genes (mTNF-α, mbIL-21, 4-1BBL). Particularly, the proliferation rate of natural killer cells increased as much as 957-fold when co-cultured with the Hut78 cell line transduced with the genes mbIL-21/4-1BBL and increased as much as 1,138-fold when co-cultured with the Hut78 cell line transduced with the genes mTNF-α/mbIL-21/4-1BBL (Table 6, FIG. 2a).

TABLE 6

| Hut78 + transduced gene(s) | Average | STDEV |
| --- | --- | --- |
| Hut78 parental | 92.7 | 90.4 |
| mTNF-α | 112.3 | 67.2 |
| mbIL-21 | 448.1 | 251.4 |
| OX40L | 50.5 | 30.7 |
| 4.1BBL | 274.9 | 189.6 |
| mTNF-α + OX40L | 204.5 | 123.2 |
| mTNF-α + 4.1BBL | 389.1 | 352.1 |
| mbIL-21 + OX40L | 372.0 | 189.2 |
| mbIL-21 + 4.1BBL | 957.0 | 537.4 |
| mTNF-α + mbIL21 + 4.1BBL | 1138.5 | 192.0 |
| mTNF-α + OX40L + mbIL21 + 4.1BBL | 823.1 | 330.0 |

When co-cultured with the non-transgenic H9 cell line, the proliferation rate increased 13-fold. In contrast, when co-cultured with the H9 cell line transduced with mbIL-21/4-1BBL and mTNF-α/mbIL-21/4-1BBL, the proliferation rates increased as much as 367- and 979-fold, respectively (Table 7 and FIG. 2b).

TABLE 7

| H9 + transduced gene(s) | Average | STDEV |
| --- | --- | --- |
| H9 parental | 12.6 | 4.3 |
| mbIL21 + 4.1BBL | 367.4 | 80.1 |
| mTNF-α + mbIL21 + 4.1BBL | 978.8 | 287.7 |

When co-cultured with other cell lines (Jurkat cell line and Peer cell line), the culture could be continued until day 11 of culture. Relatively high proliferation rates were observed in the cell lines transduced with the genes mbIL-21/4.1BBL or the genes mTNF-α/mbIL-21/4-1BBL (Tables 8 and 9, FIGS. 2c and 2b)

TABLE 8

| Jurkat + transduced gene(s) | Average (after culture for 11 days) | STDEV |
| --- | --- | --- |
| Jurkat Parental | 0.9 | 0.7 |
| mbIL21 + 4.1BBL | 36.3 | 4.8 |
| mTNF-α + mbIL21 + 4.1BBL | 43.6 | 6.6 |

TABLE 9

| Peer + transduced gene(s) | Average (after culture for 11 days) | STDEV |
| --- | --- | --- |
| Peer Parental | 1.6 | 0.7 |
| mbIL21 + 4.1BBL | 14.3 | 4.1 |

The above results reveal that natural killer cells could be cultured at a higher proliferation rate from the CD3(−) cells isolated from cord blood mononuclear cells for 21 days when the transgenic feeder cells were used than when non-transgenic feeder cells were used.

Example 3.3. Restimulation of Culture of Natural Killer Cells Using the Hut78 Cells Transduced with the Genes mTNF-α/mbIL-21/4-1BBL The transgenic T cells prepared in Example 2 were recovered from the culture flask and centrifuged at 1,200 rpm and 4° C. for 5 min. Thereafter, the cells were suspended in CellGro medium and counted using an ADAM cell counter system. The transgenic T cells were suspended to a density of $2.5 \times 10^6$ cells/ml in CellGro medium and were then inactivated by irradiation with gamma-rays at 20,000 cGy.

Natural killer cells were cultured by the following procedure. First, 1,000 IU of IL-2 and 10 ng/ml OKT-3 were plated in a plastic culture plate. On day 0 of culture, the CD3(−) cord blood mononuclear cells and the transgenic T cells (each 0.25-1 ml) were added in a ratio of 1:2.5 and 0.25-1 ml of CellGro medium supplemented with 2% (v/v) human plasma was added. Cells were cultured statically in an incubator at 37° C. for 4 days.

On day 4 of culture, the equal amount of CellGro medium supplemented with 1% (v/v) human plasma and 1,000 IU/ml IL-2 was added, followed by stationary culture. Thereafter, cells were counted at intervals of 2-3 days. CellGro medium supplemented with 1% (v/v) human plasma and 1,000 IU/ml IL-2 was added and culture was continued such that the cell density was $1 \times 10^6$ cells/ml.

For restimulation, Hut78 cells transduced with mTNF-α/mbIL-21/4-1BBL were used in the same ratio on day 0 of culture. On day 16 of culture, the first restimulation was performed. First, the cultured natural killer cells were counted using an ADAM cell counter system and diluted to $1.5 \times 10^6$ cells/ml with CellGro medium. 0.25 ml of the dilution was plated in a plastic culture plate. The Hut78 cells transduced with the genes mTNF-α/mbIL-21/4-1BBL were suspended to $2.5 \times 10^6$ cells/ml in CellGro medium and were then inactivated by irradiation with gamma-rays at 10,000 cGy.

0.25 ml of the Hut78 cells transduced with the inactivated genes mTNF-α/mbIL-21/4-1BBL were plated in a plastic culture plate. 1000 IU/ml IL-2, 10 ng/ml of OKT-3, and 1% (v/v) human plasma were added to the plastic culture plate, followed by stationary culture in an incubator at 37° C. for 3 days. Thereafter, the cell number was measured at intervals of 2-3 days. Culture was continued in CellGro medium supplemented with 1% (v/v) human plasma and 1000 IU/ml IL-2 until the cell number reached $1 \times 10^6$ cells/ml. After the first restimulation, restimulation was performed through the feeder cells at intervals of 14 days (on days 32, 46, and 60) in the same manner as described above. Culture was continued until day 70.

As a result, the proliferation rate of natural killer cells increased $6.9 \times 10^4$-fold on day 32 of culture after the first restimulation, $3.7 \times 10^6$-fold on day 46 of culture after the second restimulation, $2.3 \times 10^8$-fold on day 60 of culture after the third restimulation, and $5.9 \times 10^9$-fold on day 70 of culture after the fourth restimulation. That is, natural killer cells persistently proliferated at high rates (Table 10, FIG. 2e).

TABLE 10

| Days of culture | Average | STDEV |
| --- | --- | --- |
| 32 | $6.9 \times 10^4$ | $3.2 \times 10^3$ |
| 46 | $3.7 \times 10^6$ | $3.1 \times 10^5$ |
| 60 | $2.3 \times 10^8$ | $1.4 \times 10^8$ |
| 70 | $5.9 \times 10^9$ | $1.1 \times 10^8$ |

The results in Table 10 reveal that the periodic restimulations with the Hut78 cell line transduced with the genes mTNF-α/mbIL-21/4-1BBL led to a continuous increase in proliferation factor, demonstrating that cells of the Hut78 cell line are very suitable as feeder cells.

Experimental Example 1. Confirmation of Cell Viability of Natural Killer Cells Depending on the Transduced Gene The in-vitro cell viabilities were compared and evaluated using an ADAM cell counter system. The ADAM cell counter system is a cell counter that uses PI staining solution capable of binding to cell nuclei. The number of viable cells was calculated by subtracting the number of dead cells from the total number of counted cells. Cell viability was calculated using the following equation I.

Cell viability (%)=(Number of viable cells/total number of counted cells)×100  [Equation I]

When co-cultured with the transgenic Hut78 cell line, the viabilities of natural killer cells were around 90% regardless of whether the cell line was transduced with genes (Table 11, FIG. 3a).

TABLE 11

| Hut78 + transduced gene(s) | Average | STDEV |
|---|---|---|
| Parental | 91 | 2.6 |
| mTNF-α | 92.8 | 2.1 |
| mbIL-21 | 92.8 | 1.5 |
| OX40L | 90.3 | 1.3 |
| 4.1BBL | 91.3 | 1.3 |
| mTNF-α + OX40L | 93.5 | 1.7 |
| mTNF-α + 4.1BBL | 92.5 | 1.7 |
| mbIL-21 + OX40L | 89 | 2.4 |
| mbIL-21 + 4.1BBL | 89.8 | 2.6 |
| mTNF-α + mbIL-21 + 4.1BBL | 89 | 3.4 |
| QD | 88.5 | 3.4 |

When cultured in the H9, Jurkat, and Peer cell lines transduced with the gene mbIL-21/4-1BBL and the genes mTNF-α/mbIL-21/4-1BBL, the cell viabilities of natural killer cells were >90% on day 21 of culture (H9) and day 11 of culture (Jurkat, Peer) (Tables 12 to 14, FIGS. 3b to 3d).

TABLE 12

| H9 + transduced gene(s) | Average | STDEV |
|---|---|---|
| Parental | 86 | 6.1 |
| mbIL21 + 44.1BBL | 91 | 3.1 |
| mTNF-α + mbIL21 + 4.1BBL | 94 | 0.6 |

TABLE 13

| Jurkat + transduced gene(s) | Average | STDEV |
|---|---|---|
| Parental | 80 | 6.1 |
| mbIL21 + 4.1BBL | 91 | 0.6 |
| mTNF-α + mbIL21 + 4.1BBL | 92 | 2.0 |

TABLE 14

| Peer + transduced gene(s) | Average | STDEV |
|---|---|---|
| Parental | 83.5 | 6.1 |
| mbIL21 + 4.1BBL | 91 | 0.6 |

Natural killer cells were cultured in the Hut78 cell line transduced with the genes mTNF-α/mbIL-21/4-1BBL with increasing number of restimulations. As a result, the viabilities of natural killer cells were >~90% despite the increasing number of restimulations (Table 15, FIG. 3e).

TABLE 15

| Days of culture | 32 | 42 | 60 | 70 |
|---|---|---|---|---|
| Average | 96.0 | 93.5 | 97.5 | 91.5 |
| STDEV | 1.4 | 0.7 | 0.7 | 4.9 |

These results reveal that the viability of natural killer cells was maintained at a high level even during continued culture for a long period of time, offering the possibility of long-term expansion culture of natural killer cells.

Experimental Example 2. Confirmation of Purity of Natural Killer Cells

Natural killer cells cultured for 21 days or natural killer cells cultured by repeated restimulations were collected and centrifuged at 1,200 rpm for 5 min. The culture solution was removed by suction. Cells were counted after dilution with 1 ml of the FACS buffer. Cells were diluted to $5 \times 10^6$ cells/ml with the FACS buffer. The diluted cell solution was added to 5 ml FACS tubes (Falcon, 352052) (100 μl per tube). The phenotypes of the cells were analyzed with the following antibodies:

Tube 1: anti-human CD3-FITC (BD Pharmingen, 555332), anti-human CD16-PE (BD Pharmingen, 555407), anti-human CD56-BV421 (BD Pharmingen, 562751)

Tube 2: anti-human CD14-FITC (BD Pharmingen, 555397), anti-human CD19-PE (BD Pharmingen, 555413), anti-human CD3-BV421 (BD Pharmingen, 562438)

Tube 3: anti-human CD3-FITC, anti-human NKG2D-PE (R&D system, FAB139P), anti-human CD56-BV421

Tube 4: anti-human CD3-FITC, anti-human NKp30-PE (BD Pharmingen, 558407), anti-human CD56-BV421

Tube 5: anti-human CD3-FITC, anti-human NKp44-PE (BD Pharmingen, 558563), anti-human CD56-BV421

Tube 6: anti-human CD3-FITC, anti-human NKp46-PE (BD Pharmingen, 557991), anti-human CD56-BV421

Tube 7: anti-human CD3-FITC, anti-human DNAM-1-PE (BD Pharmingen, 559789), anti-human CD56-BV421

Tube 8: anti-human CD3-FITC, anti-human CXCR3-PE (BD Pharmingen, 557185), anti-human CD56-BV421

Tube 9: anti-human CD3-FITC, PE mouse IgG1 κ isotype control (BD Pharmingen, 555749), anti-human CD56-BV421

Tube 10: FITC mouse IgG1 κ isotype control (BD Pharmingen, 555748), PE mouse IgG1 κ isotype control, BV421 mouse IgG1 κ isotype control (BD Pharmingen, 562438)

The cells in each tube were stained with one of the three fluorescent antibodies. Specifically, the cells in Tube 1 were stained with the anti-human CD56 antibody, the cells in Tube 2 were stained with the anti-human CD3 antibody, the cells in Tubes 3-9 were stained with the anti-human CD56 antibody, and the cells in Tube 10 were stained with the isotype control antibody.

The cells in the tubes were stained at a refrigeration temperature for 30 min. Thereafter, 2 ml of the FACS buffer was added to the stained cells, followed by centrifugation at 1,500 rpm for 3 min. The supernatant was discarded, 2 ml FACS buffer was added, followed by centrifugation at 2,000 rpm for 3 min. After removal of the supernatant, cells were suspended in 200 μl of cytofix buffer (fixation buffer, BD, 554655) and were then identified and examined for purity and phenotype using FACS LSRII Fortessa (BD Biosciences).

After co-culture of the CD3(−) cells isolated from cord blood mononuclear cells with the transgenic Hut78 cell line for 21 days, natural killer cells were identified and analyzed for purity. As a result, the contents of natural killer cells (CD3−CD56+) were found to be >90% in all conditions irrespective of whether the cell line was transduced with genes (Table 16, FIG. 4a).

TABLE 16

| Hut78 + transduced gene(s) | Average | STDEV |
| --- | --- | --- |
| Parental | 92.4 | 9.6 |
| mTNF-α | 96.8 | 2.5 |
| mbIL-21 | 98.6 | 0.9 |
| OX40L | 95.7 | 3.6 |
| 4.1BBL | 98 | 1.8 |
| mTNF-α + OX40L | 97.2 | 2.5 |
| mTNF-α + 4.1BBL | 98.6 | 1 |
| mbIL-21 + OX40L | 98.4 | 1.3 |
| mbIL-21 + 4.1BBL | 98.5 | 0.9 |
| mTNF-α + mbIL-21 + 4.1BBL | 98.7 | 0.9 |
| QD | 99.3 | 0.5 |

After co-culture with the H9, Jurkat or Peer cell line transduced with the genes mbIL-21/4-1BBL or mTNF-α/mbIL-21/4-1BBL, the cultured natural killer cells were identified and measured for purity. As a result, the purities of the natural killer cells produced by co-culture with the transgenic cell lines were maintained at higher levels than those by co-culture with the non-transgenic cell lines (Tables 17 to 19, FIGS. 4b to 4d).

TABLE 17

| H9 + transduced gene(s) | Average | STDEV |
| --- | --- | --- |
| Parental | 91.5 | 4.1 |
| mbIL21 + 4.1BBL | 98.5 | 0.7 |
| mTNF-α + mbIL21 + 4.1BBL | 99 | 0.3 |

TABLE 18

| Jurkat + transduced gene(s) | Average | STDEV |
| --- | --- | --- |
| Parental | 88.6 | 6.9 |
| mbIL21 + 4.1BBL | 97.6 | 1.3 |
| mTNF-α + mbIL21 + 4.1BBL | 97.5 | 0.8 |

TABLE 19

| Peer + transduced gene(s) | Average | STDEV |
| --- | --- | --- |
| Parental | 79.2 | 14.6 |
| mbIL21 + 4.1BBL | 94.9 | 2.1 |

Natural killer cells were cultured while increasing the number of restimulations with the cell lines transduced with the three genes mTNF-α/mbIL-21/4-1BBL. The contents of the natural killer cells (CD3−CD56+) were found to be high (>90%) until day 60 of culture (Table 20, FIG. 4e).

TABLE 20

| Days of culture | 32 | 60 |
| --- | --- | --- |
| Average | 99.7 | 97.8 |
| STDEV | 0.1 | 0.8 |

Experimental Example 3. Analysis of Activation Markers of Natural Killer Cells

After co-culture of the CD3(−) cells isolated from cord blood mononuclear cells with the transgenic feeder cells for 21 days, the expressions of representative receptors of natural killer cells were analyzed.

When co-cultured with the Hut78 cell line, all CD16 cells were expressed at high levels. Activation markers NKG2D, NKp30, NKp44, NKp46, and DNAM-1 were expressed at higher levels without variations between donors when the feeder cells were transduced with double genes than when the feeder cells were not transduced or transduced with single genes (FIGS. 5a to 5g).

The expression levels of CD16, NKG2D, DNAM-1, and CXCR3 were found to be higher when co-cultured with the feeder cells of the non-transgenic H9 cell line than when co-cultured with the feeder cells transduced with the genes mbIL-21/4-1BBL or the triple genes mTNF-α/mbIL-21/4-1BBL. The expression levels of other activation markers NKp30, NKp44, and NKp46 were found to be high without variations between donors. In conclusion, the feeder cells transduced with double and triple genes are useful in increasing the activity and tumor targeting ability of NK cells (FIGS. 6a to 6g).

Natural killer cells were produced by restimulating the co-culture using the Hut78 cell line transduced with the triple genes mTNF-α/mbIL-21/4-1BBL, and their phenotypes were identified. As a result, the expressions of activation markers, including NKG2D, NKp44, NKp46, DNAM-1, and CXCR3, showed a tendency to decrease when the restimulation was performed 4 times during culture compared to when the restimulation was performed only once. These results revealed that the increasing number of restimulations led to a long culture period, which affected the expression levels of some of the activation markers (FIGS. 7a and 7b).

Experimental Example 4. Confirmation of Cytotoxicities of Natural Killer Cells Depending on Genes Transduced into T Cells and Co-Culture with T Cells $1 \times 10^6$ cells of the K562 cancer cell were placed in a 15 ml tube and centrifuged. The cell pellets were suspended in RPMI1640 medium supplemented with 1 ml of 10% (v/v) FBS. After addition of 30 µl of 1 mM Calcein-AM (Molecular probe, C34852), the suspension was protected from light with aluminum foil, followed by staining in an incubator at 37° C. for 1 h.

The Calcein-AM stained tumor cell line was washed in RPMI1640 medium supplemented with 10-15 ml of 10% (v/v) FBS and centrifuged. The pellets were suspended to a density of $1 \times 10^5$ cells/ml in RPMI1640 medium supplemented with 10 ml of 10% (v/v) FBS. $1 \times 10^6$ natural killer cells were placed in a 15 ml tube and centrifuged. The pellets in a desired ratio (1:1) to the K562 cancer cell line were suspended in RPMI1640 medium supplemented with 10% (v/v) FBS. A mixture of the K562 cancer cell line and the natural killer cell line (each 100 µl) were plated in a 96-well U-bottom plate (Nunc, 163320). Fluorescence was measured in triplicate for each well and the measured values were averaged.

The stained K562 cancer cell line was added to spontaneous release wells (100 µl/well) and RPMI1640 medium supplemented with 10% (v/v) FBS was added thereto (100 µl/well). The stained K562 cancer cell line was added to maximum release wells (100 µl/well) and triple-distilled water containing 2% (v/v) Triton-X 100 was added thereto (100 µl/well).

The auto-fluorescence values of the RPMI1640 medium supplemented with 10% (v/v) FBS and the RPMI1640 medium supplemented with 2% (v/v) Triton-X 100 were corrected by subtracting the fluorescence value of a mixture of 100 μl of RPMI1640 medium supplemented with 10% (v/v) FBS and 100 μl of RPMI1640 medium supplemented with 2% (v/v) Triton-X 100 from the fluorescence value of 200 μl of RPMI1640 medium supplemented with 10% (v/v) FBS and adding the difference A to the maximum release value.

Incubation was allowed to proceed in an incubator at 37° C. for 4 h in the dark and the plate was then centrifuged at 2,000 rpm for 3 min. The supernatant was plated in a 96-well black plate (Nunc, 237108) (100 μl per well). The fluorescence value ($OD_{480/535}$ nm) was measured using a fluorescent plate reader (Perkin Elmer, VICTOR X3) and the cytotoxicity (% of killing) of natural killer cells to tumor cells was calculated using the following equation II:

% of killing=(average fluorescence value of sample well−average fluorescence value of spon. well)/[(average fluorescence value of max. well+$A$)− average fluorescence value of spon. well]×100   [Equation II]

The direct cytotoxicities of natural killer cells cultured using various types of feeder cells to the K562 cancer cell line were measured. As a result, the cytotoxicities of natural killer cells cultured using feeder cells transduced with the genes mbIL-21/4-1BBL gene and feeder cells transduced with the genes mTNF-α/mbIL-21/4-1BBL were higher than those of natural killer cells cultured using non-transgenic feeder cells (FIGS. 8a to 8d).

The cytotoxicity of natural killer cells was maintained high without a significant difference until day 60 of culture despite the increasing number of restimulations with the Hut78 cell line transduced with the genes mTNF-α/mbIL-21/4-1BBL (FIG. 8e).

These results concluded that the feeder cells transduced with the genes mbIL-21/4-1BBL or the genes mTNF-α/mbIL-21/4-1BBL are useful in ex vivo expansion culture of high-purity natural killer cells with high cytotoxicity and activity than the non-transgenic feeder cells.

The invention claimed is:

1. A method for expanding natural killer cells, the method comprising:

co-culturing seed cells comprising cord blood-derived natural killer cells with a first population of feeder cells, wherein the first population of feeder cells comprises genetically engineered CD4+ T cells expressing a 4-1BBL polypeptide, a membrane-bound IL-21 polypeptide, and a TNF-α polypeptide comprising a mutated Tumor Necrosis Factor-α Converting Enzyme (TACE) recognition site, wherein the seed cells and genetically engineered CD4+ T cells are co-cultured in a medium comprising: 1,000 ng/ml of an anti-CD3 antibody; and IL-2, thereby expanding the natural killer cells;

wherein the seed cells comprise mononuclear cells derived from cord blood; and wherein the seed cells are depleted of CD3(+) cells.

2. The method of claim 1, wherein the genetically engineered CD4+ T cells are cells from a cell line selected from the group consisting of Jurkat, Peer, H9 and HuT78.

3. The method of claim 2, wherein the genetically engineered CD4+ T cells are cells from a HuT78 cell line.

4. The method of claim 1, wherein the 4-1BBL polypeptide comprises an amino acid sequence of SEQ ID NO: 1.

5. The method of claim 1, wherein the membrane-bound IL-21 polypeptide comprises an amino acid sequence of SEQ ID NO: 3.

6. The method of claim 1, wherein the TNF-α polypeptide comprises an amino acid sequence of SEQ ID NO: 8.

7. The method of claim 1, wherein the method comprises mixing the genetically engineered CD4+ T cells and the seed cells at a ratio of between 0.1:1 and 50:1.

8. The method of claim 1, wherein the method comprises co-culturing the genetically engineered CD4+ T cells and the seed cells for 5-60 days.

9. The method of claim 8, wherein the method comprises co-culturing the genetically engineered CD4+ T cells and the seed cells for 14-21 days.

10. The method of claim 1, wherein the method further comprises co-culturing the seed cells with a second population of feeder cells.

11. The method of claim 1, wherein the 4-1BBL polypeptide comprises an amino acid sequence of SEQ ID NO: 1, the membrane-bound IL-21 polypeptide comprises an amino acid sequence of SEQ ID NO: 3, and the TNF-a polypeptide comprises an amino acid sequence of SEQ ID NO: 8.

* * * * *

SEQUENCE LISTING

<160> NUMBER OF SEQ ID NOS: 25

<210> SEQ ID NO 1
<211> LENGTH: 254
<212> TYPE: PRT
<213> ORGANISM: Artificial Sequence
<220> FEATURE:
<223> OTHER INFORMATION: amino acid seqeunce for 4-1BBL

<400> SEQUENCE: 1

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
            85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220
```

```
Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
            245                 250
```

<210> SEQ ID NO 2
<211> LENGTH: 765
<212> TYPE: DNA
<213> ORGANISM: Artificial Sequence
<220> FEATURE:
<223> OTHER INFORMATION: nucleotide sequence of 4-1BBL

<400> SEQUENCE: 2

```
atggaatacg cctctgacgc ttcactggac cccgaagccc cgtggcctcc cgcgccccgc      60
gctcgcgcct gccgcgtact gccttgggcc ctggtcgcgg ggctgctgct gctgctgctg     120
ctcgctgccg cctgcgccgt cttcctcgcc tgccctggg ccgtgtccgg ggctcgcgcc      180
tcgcccggct ccgcggccag cccgagactc cgcgagggtc ccgagctttc gcccgacgat     240
cccgccggcc tcttggacct gcggcagggc atgtttgcgc agctggtggc ccaaaatgtt     300
ctgctgatcg atgggcccct gagctggtac agtgacccag gcctggcagg cgtgtccctg     360
acgggggggcc tgagctacaa agaggacacg aaggagctgg tggtggccaa ggctggagtc     420
tactatgtct tctttcaact agagctgcgg cgcgtggtgg ccggcgaggg ctcaggctcc     480
gtttcacttg cgctgcacct gcagccactg cgctctgctg ctggggccgc cgccctggct     540
ttgaccgtgg acctgccacc cgcctcctcc gaggctcgga actcggcctt cggtttccag     600
ggccgcttgc tgcacctgag tgccggccag cgcctgggcg tccatcttca cactgaggcc     660
agggcacgcc atgcctggca gcttacccag ggcgccacag tcttgggact cttccgggtg     720
accccccgaaa tcccagccgg actcccttca ccgaggtcgg aataa                    765
```

<210> SEQ ID NO 3
<211> LENGTH: 223
<212> TYPE: PRT
<213> ORGANISM: Artificial Sequence
<220> FEATURE:
<223> OTHER INFORMATION: amino acid seqeunce for membrane bound IL-21
      (mbIL-21)

<400> SEQUENCE: 3

```
Met Ala Leu Pro Val Thr Ala Leu Leu Leu Pro Leu Ala Leu Leu Leu
1               5                   10                  15

His Ala Ala Arg Pro Gln Asp Arg His Met Ile Arg Met Arg Gln Leu
                20                  25                  30

Ile Asp Ile Val Asp Gln Leu Lys Asn Tyr Val Asn Asp Leu Val Pro
            35                  40                  45

Glu Phe Leu Pro Ala Pro Glu Asp Val Glu Thr Asn Cys Glu Trp Ser
        50                  55                  60

Ala Phe Ser Cys Phe Gln Lys Ala Gln Leu Lys Ser Ala Asn Thr Gly
65                  70                  75                  80

Asn Asn Glu Arg Ile Ile Asn Val Ser Ile Lys Lys Leu Lys Arg Lys
                85                  90                  95

Pro Pro Ser Thr Asn Ala Gly Arg Arg Gln Lys His Arg Leu Thr Cys
            100                 105                 110

Pro Ser Cys Asp Ser Tyr Glu Lys Lys Pro Pro Lys Glu Phe Leu Glu
        115                 120                 125

Arg Phe Lys Ser Leu Leu Gln Lys Met Ile His Gln His Leu Ser Ser
    130                 135                 140
```

Arg Thr His Gly Ser Glu Asp Ser Ala Lys Pro Thr Thr Pro Ala
145                 150                 155                 160

Pro Arg Pro Pro Thr Pro Ala Pro Thr Ile Ala Ser Gln Pro Leu Ser
            165                 170                 175

Leu Arg Pro Glu Ala Cys Arg Pro Ala Ala Gly Gly Ala Val His Thr
        180                 185                 190

Arg Gly Leu Asp Phe Ala Cys Asp Ile Tyr Ile Trp Ala Pro Leu Ala
            195                 200                 205

Gly Thr Cys Gly Val Leu Leu Leu Ser Leu Val Ile Thr Leu Tyr
    210                 215                 220

<210> SEQ ID NO 4
<211> LENGTH: 672
<212> TYPE: DNA
<213> ORGANISM: Artificial Sequence
<220> FEATURE:
<223> OTHER INFORMATION: nucleotide sequence of membrane bound IL-21
      (mbIL-21)

<400> SEQUENCE: 4
atggctctgc cgtcaccgc tctgctgctg cctctggccc tgctgctgca cgccgcaaga      60
ccacaggacc gccacatgat tcggatgagg cagctgatcg acattgtgga tcagctgaag     120
aactacgtga atgacctggt ccccgagttc ctgcccgctc ctgaggatgt cgaaacaaac     180
tgcgaatggt ctgcattcag ttgttttcag aaggctcagc tgaaatctgc aaacactgga     240
aacaatgagc gaatcattaa tgtgagcatc aagaaactga agcggaaacc cccttccact     300
aatgcaggcc ggagacagaa gcaccgactg acctgcccct catgtgacag ctatgaaaag     360
aaaccaccca agagttcct ggagcggttc aagagcctgc tccagaaaat gatccaccag     420
cacctgagca gccggaccca cggcagcgag gattctgcca gcctaccac aactccagct     480 ccccgccctc aaccctgc accaacaatt gccagtcagc cctgtcact gaggcctgaa      540 gcatgccgcc cagccgctgg cggagcagtc cacacacgag gcctggactt tgcttgtgat     600
atctacattt gggcacctct ggctggaact tgcggcgtcc tgctgctgtc cctggtcatc     660
accctgtatt ga                                                         672

<210> SEQ ID NO 5
<211> LENGTH: 183
<212> TYPE: PRT
<213> ORGANISM: Artificial Sequence
<220> FEATURE:
<223> OTHER INFORMATION: amino acid seqeunce for OX40L

<400> SEQUENCE: 5

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

```
Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
        130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 6
<211> LENGTH: 552
<212> TYPE: DNA
<213> ORGANISM: Artificial Sequence
<220> FEATURE:
<223> OTHER INFORMATION: nucleotide sequence of OX40L

<400> SEQUENCE: 6
atggaacggg tgcaacctct ggaggagaat gtgggcaatg cagcccggcc aagatttgag      60
aggaacaagc tactgctggt ggcctctgtg atacagggac tggggctcct cctgtgcttc     120
acctacatct gcctgcactt cagcgctctt caggtgtcac accggtatcc ccgcatacaa     180
agtatcaagg tccagtttac cgagtataag aaagagaagg gtttcatcct cactagtcag     240
aaggaggatg aaatcatgaa ggtgcagaac aactcagtta ttattaactg tgacggcttt     300
tatctgatca gcctgaaggg ctacttctcc caggaagtaa acatcagcct gcattaccag     360
aaggatgagg agcccctgtt tcagctgaag aaggtccggt ccgtgaactc ccttatggtc     420
gcctctctga cgtacaagga caaggtgtac ctcaatgtga ccacagacaa tacatccctg     480
gatgacttcc atgtgaatgg cggagaactg attctgattc accagaaccc tggggagttc     540
tgtgtcttgt ga                                                        552

<210> SEQ ID NO 7
<211> LENGTH: 705
<212> TYPE: DNA
<213> ORGANISM: Homo sapiens

<400> SEQUENCE: 7
atgagcactg aaagcatgat ccgggacgtg gagctggccg aggaggcgct ccccaagaag      60 acagggggc cccagggctc caggcggtgc ttgttcctca gcctcttctc cttcctgatc     120
gtggcaggcg ccaccacgct cttcgcctg ctgcactttg gagtgatcgg ccccagagg      180 gaagagttcc caggaccct ctctctaatc agccctctgg cccaggcagt cagatcatct     240
tctcgaaccc cgagtgacaa gcctgtagcc catgttgtag caaaccctca agctgagggg     300
cagctccagt ggctgaaccg ccgggccaat gccctcctgg ccaatggcgt ggagctgaga     360
gataaccagc tggtggtgcc atcagagggc ctgtacctca tctactccca ggtcctcttc     420
aagggccaag ctgccctc cacccatgtg ctcctcaccc acaccatcag ccgcatcgcc     480
gtctcctacc agaccaaggt caacctcctc tctgccatca gagcccctg ccagagggag     540 accccagagg gggctgaggc caagccctgg tatgagccca tctatctggg aggggtcttc     600
cagctggaga agggtgaccg actcagcgct gagatcaatc ggcccgacta tctcgacttt     660
gccgagtctg ggcaggtcta ctttgggatc attgccctgt gagga                    705
```

<210> SEQ ID NO 8
<211> LENGTH: 233
<212> TYPE: PRT
<213> ORGANISM: Artificial Sequence
<220> FEATURE:
<223> OTHER INFORMATION: amino acid seqeunce for mutated TNF alpha
      (mTNF-a)

<400> SEQUENCE: 8

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Pro Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 9
<211> LENGTH: 702
<212> TYPE: DNA
<213> ORGANISM: Artificial Sequence
<220> FEATURE:
<223> OTHER INFORMATION: nucleotide sequence of mutated TNF alpha
      (mTNF-a)

<400> SEQUENCE: 9

```
atgagcactg aaagcatgat ccgggacgtg gagctggccg aggaggcgct ccccaagaag     60
acaggggggc cccagggctc caggcggtgc ttgttcctca gcctcttctc cttcctgatc    120
gtggcaggcg ccaccacgct cttctgcctg ctgcactttg gagtgatcgg cccccagagg    180
gaagagttcc ccagggacct ctctctaatc agccctctgg cccagccggt cagatcatct    240
tctcgaaccc cgagtgacaa gcctgtagcc catgttgtag caaaccctca agctgagggg    300
cagctccagt ggctgaaccg ccgggccaat gccctcctgg ccaatggcgt ggagctgaga    360
```

```
gataaccagc tggtggtgcc atcagagggc ctgtacctca tctactccca ggtcctcttc    420
aagggccaag gctgcccctc cacccatgtg ctcctcaccc acaccatcag ccgcatcgcc    480
gtctcctacc agaccaaggt caacctcctc tctgccatca agagcccctg ccagagggag    540
accccagagg gggctgaggc caagccctgg tatgagccca tctatctggg aggggtcttc    600
cagctggaga agggtgaccg actcagcgct gagatcaatc ggcccgacta tctcgacttt    660
gccgagtctg ggcaggtcta ctttgggatc attgccctgt ga                      702
```

```
<210> SEQ ID NO 10
<211> LENGTH: 46
<212> TYPE: DNA
<213> ORGANISM: Artificial Sequence
<220> FEATURE:
<223> OTHER INFORMATION: Forward primer for 4-1BBL (PCR)

<400> SEQUENCE: 10
tctagagcta gcgaattcgc caccatggaa tacgcctctg acgctt              46
```

```
<210> SEQ ID NO 11
<211> LENGTH: 38
<212> TYPE: DNA
<213> ORGANISM: Artificial Sequence
<220> FEATURE:
<223> OTHER INFORMATION: Reverse primer for 4-1BBL (PCR)

<400> SEQUENCE: 11
ttcgcggccg cggatcctta ttccgacctc ggtgaagg                       38
```

```
<210> SEQ ID NO 12
<211> LENGTH: 40
<212> TYPE: DNA
<213> ORGANISM: Artificial Sequence
<220> FEATURE:
<223> OTHER INFORMATION: Forward primer for mbIL-21 (PCR)

<400> SEQUENCE: 12
tagagctagc gaattcgcca ccgccaccat ggctctgccc                     40
```

```
<210> SEQ ID NO 13
<211> LENGTH: 35
<212> TYPE: DNA
<213> ORGANISM: Artificial Sequence
<220> FEATURE:
<223> OTHER INFORMATION: Reverse primer for mbIL-21 (PCR)

<400> SEQUENCE: 13
tcgcggccgc ggatcctcaa tacagggtga tgacc                          35
```

```
<210> SEQ ID NO 14
<211> LENGTH: 38
<212> TYPE: DNA
<213> ORGANISM: Artificial Sequence
<220> FEATURE:
<223> OTHER INFORMATION: Forward primer for OX40L (PCR)

<400> SEQUENCE: 14
tagagctagc gaattcgcca ccatggaacg ggtgcaac                       38
```

```
<210> SEQ ID NO 15
<211> LENGTH: 37
<212> TYPE: DNA
<213> ORGANISM: Artificial Sequence
<220> FEATURE:
```

<223> OTHER INFORMATION: Reverse primer for OX40L (PCR)

<400> SEQUENCE: 15
tcgcggccgc ggatcctcac aagacacaga actcccc					37

<210> SEQ ID NO 16
<211> LENGTH: 40
<212> TYPE: DNA
<213> ORGANISM: Artificial Sequence
<220> FEATURE:
<223> OTHER INFORMATION: Forward primer for mTNF-a (PCR)

<400> SEQUENCE: 16
tagagctagc gaattcgcca ccgccaccat ggctctgccc					40

<210> SEQ ID NO 17
<211> LENGTH: 34
<212> TYPE: DNA
<213> ORGANISM: Artificial Sequence
<220> FEATURE:
<223> OTHER INFORMATION: Reverse primer for mTNF-a (PCR)

<400> SEQUENCE: 17
tcgcggccgc ggatcctcac agggcaatga tccc					34

<210> SEQ ID NO 18
<211> LENGTH: 20
<212> TYPE: DNA
<213> ORGANISM: Artificial Sequence
<220> FEATURE:
<223> OTHER INFORMATION: Forward primer for 4-1BBL (RT-qPCR)

<400> SEQUENCE: 18
tctgagacag ggcatgtttg					20

<210> SEQ ID NO 19
<211> LENGTH: 20
<212> TYPE: DNA
<213> ORGANISM: Artificial Sequence
<220> FEATURE:
<223> OTHER INFORMATION: Reverse primer for 4-1BBL (RT-qPCR)

<400> SEQUENCE: 19
ccaccagttc tttggtgtcc					20

<210> SEQ ID NO 20
<211> LENGTH: 20
<212> TYPE: DNA
<213> ORGANISM: Artificial Sequence
<220> FEATURE:
<223> OTHER INFORMATION: Forward primer for mTNF-a (RT-qPCR)

<400> SEQUENCE: 20
aacctcctct ctgccatcaa					20

<210> SEQ ID NO 21
<211> LENGTH: 20
<212> TYPE: DNA
<213> ORGANISM: Artificial Sequence
<220> FEATURE:
<223> OTHER INFORMATION: Reverse primer for mTNF-a (RT-qPCR)

<400> SEQUENCE: 21
atagtcgggc cgattgatct					20

```
<210> SEQ ID NO 22
<211> LENGTH: 20
<212> TYPE: DNA
<213> ORGANISM: Artificial Sequence
<220> FEATURE:
<223> OTHER INFORMATION: Forward primer for mbIL-21 (RT-qPCR)

<400> SEQUENCE: 22
tggaaacaat gagcgaatca                                               20

<210> SEQ ID NO 23
<211> LENGTH: 20
<212> TYPE: DNA
<213> ORGANISM: Artificial Sequence
<220> FEATURE:
<223> OTHER INFORMATION: Reverse primer for mbIL-21 (RT-qPCR)

<400> SEQUENCE: 23
aaccgctcca ggaactcttt                                               20

<210> SEQ ID NO 24
<211> LENGTH: 20
<212> TYPE: DNA
<213> ORGANISM: Artificial Sequence
<220> FEATURE:
<223> OTHER INFORMATION: Forward primer for hTOP1 (RT-qPCR)

<400> SEQUENCE: 24
ccagacggaa gctcggaaac                                               20

<210> SEQ ID NO 25
<211> LENGTH: 22
<212> TYPE: DNA
<213> ORGANISM: Artificial Sequence
<220> FEATURE:
<223> OTHER INFORMATION: Reverse primer for hTOP1 (RT-qPCR)

<400> SEQUENCE: 25
gtccaggagg ctctatcttg aa                                            22
```